United States Patent [19]
Gelfand et al.

[11] Patent Number: 5,910,417
[45] Date of Patent: Jun. 8, 1999

[54] REGULATION OF CYTOKINE PRODUCTION IN A HEMATOPOIETIC CELL

[75] Inventors: Erwin W. Gelfand, Englewood; Gary L. Johnson, Boulder, both of Colo.

[73] Assignee: National Jewish Center for Immunology and Respiratory Medicine, Denver, Colo.

[21] Appl. No.: 08/656,563

[22] Filed: May 31, 1996

[51] Int. Cl.$^6$ .......................... G01N 33/53; A01N 37/18
[52] U.S. Cl. .......................... 435/7.2; 435/7.1; 436/501; 514/2
[58] Field of Search .......................... 435/7.1, 7.2, 240.2, 435/325, 7.21; 512/2, 44; 424/85.1; 436/501

[56] References Cited

U.S. PATENT DOCUMENTS 5,378,725  1/1995  Bonjouklian et al. ................... 514/453

OTHER PUBLICATIONS

Barker et al., *Mol. Biol. of the Cell*, 1995, 6:1145–1158.
Baumgartner et al., *J. Immunol.*, 1994, 153:2609–2617.
Galli et al., *Allergy*, 1995, 50:851–862.
Gordon et al., *J. Exp. Med.*, 1991, 174:103–107.
Hamawy et al., *Cell. Signalling*, 1995, 7(6):535–544.
Hutchinsion et al., *J. Biol. Chem.*, 1995, 270(27):16333–16338.
Marquardt, et al., *J. Immunol.*, 1996, 156:1942–1945.
Raingeaud et al., *J. Biol. Chem.*, 1996, 270(13):7420–7426.
Lin et al *J. Clin. Immuno.* vol. 14(1): pp. 1–13 (1994).
Piccinni et al *Proc. Natl. Acad. Sci. USA* vol. 88: pp. 8656–8660. 1991.
Daëron et al *J. Clin. Invest.* vol. 95: pp. 577–585 (1995).
Okayama et al *J. Immuno.* vol. 155: pp. 1796–1808 (1995).

*Primary Examiner*—John Ulm
*Attorney, Agent, or Firm*—Lahive & Cockfield, LLP; Giulio A. DeConti, Jr.; Peter C. Lauro

[57] ABSTRACT

A method useful for regulating cytokine production by a hematopoietic cell by regulating an MEKK/JNKK-contingent signal transduction pathway in such a cell is disclosed. Methods of identifying compounds capable of specifically regulating an MEKK/JNKK-contingent signal transduction pathway in hematopoietic cells, a kit for identifying cytokine regulators, methods to treat diseases involving cytokine production, and cells useful in such methods are also set forth.

2 Claims, 14 Drawing Sheets

REGULATION OF CYTOKINE PRODUCTION IN A HEMATOPOIETIC CELL

GOVERNMENT RIGHTS

This invention was made in part with government support under: AI HL-36577 and DK-37871, each awarded by the National Institutes of Health. The government has certain rights to this invention.

FIELD OF THE INVENTION

The present invention relates to a method for regulating an MEKK/JNKK-contingent signal transduction pathway in a hematopoietic cell in order to regulate cytokine production by such cell.

BACKGROUND OF THE INVENTION

Aggregation of the high-affinity Fc receptors for immunoglobulin E (IgE) (FcεRI) on the surface of mast cells initiates intracellular signal transduction pathways, involving the tyrosine phosphorylation of cellular proteins, activation of phospholipase Cγ, hydrolysis of phosphoinositide, increase in intracellular calcium, activation of protein kinase C and the stimulation of phosphatidylinositol 3-kinase. These signal transduction pathways are believed to be involved in the exocytic release of inflammatory mediators such as vasoactive amines, cytokines, and lipid metabolites. The production of cytokines by mast cells is a critical event that influences the pathogenesis of allergic inflammation in asthma and other allergic disorders.

In addition to the activation of phospholipase Cγ and protein kinase C, which appears to be essential for the FcεRI-mediated release of preformed mediators, the aggregation of FcεRI on rat basophilic leukemia 2H3 (RBL-2H3) cells has been shown to induce histamine and leukotriene release. Except for the activation of the extracellular signal-regulated kinases/mitogen activated protein kinases (ERKs/MAPKs), however, the downstream consequences of early activation events in a signal transduction pathway leading to cytokine production are not well defined.

The extracellular signal-regulated kinases (ERKs), ERK1 and ERK2, are serine/threonine protein kinases that are activated through concomitant phosphorylation of tyrosine and threonine residues. Prior to the current invention, it was thought that ERKs were one of the intermediates in the signal transduction pathway leading to increases in gene transcription and proliferation, including cytokine gene transcription. ERKs phosphorylate specific transcription factors including members of the Ets family, such as Elk-1, and it has been reported that ERKs are activated via FcεRI on mast cells.

Despite the current understanding of early signal transduction events in hematopoietic cells, there remains a need to elucidate signal transduction pathways that specifically regulate cytokine production in such cells and to determine what molecules and/or functional elements of such molecules are responsible for regulating such cellular pathways. There is also a need for products and processes that permit the effective regulation of specific steps in such a signal transduction pathway. Regulation of specific steps of a signal transduction pathway which regulate cytokine production permits the implementation of predictable controls of such signal transduction in cells, thereby allowing modulation of the effects of cytokine production in diseases wherein such modulation can ameliorate disease pathogenesis.

SUMMARY OF THE INVENTION

The present invention generally relates to a method to regulate a novel signal transduction pathway to modulate the production of cytokines by a hematopoietic cell. The present inventors have identified an MEKK/JNKK-contingent signal transduction pathway which regulates the production of cytokines by a hematopoietic cell. Prior to the present invention, it was thought that signal transduction through the ERK pathway lead to increases in gene transcription and proliferation, including cytokine gene transcription. The ERK pathway is known to be distinct from the pathway of the present invention; therefore, the discovery that an ERK-independent signal transduction pathway regulates cytokine production is unexpected. The present inventors were the first to appreciate that an MEKK/JNKK-contingent signal transduction pathway, and not an ERK-dependent pathway, regulates cytokine production. Furthermore, the present inventors were the first to appreciate that such an MEKK/JNKK-contingent pathway is activated in mast cells through aggregation of FcεRI and activation of PI3-kinase (PI3-K). The present inventors were also the first to appreciate the method of regulation of such a signal transduction pathway in order to regulate production of cytokines such as, TNF-a, IL-1, IL-2, IL-3, IL-4, IL-5, IL-6, IL-7, IL-8, IL-9, IL-10, IL-11, IL-12, IL-13, IL-14, IL-15, IL-16, G-CSF, GM-CSF, TNF-b, TGF-b, IFN-γ, and IFN-α/β, in a hematopoietic cell such as a mast cell, a basophil, an eosinophil, a neutrophil, a T cell, a B cell, a macrophage, a dendritic cell, and a natural killer cell.

One embodiment of the present invention relates to a method to regulate cytokine production by regulating an MEKK/JNKK-contingent signal transduction pathway in a hematopoietic cell. Preferably, such a method comprises regulating one or more of the signal transduction molecule selected from the group of MEKK1, MEKK2, MEKK3, MEKK4, JNKK, JNK1 and JNK2.

In one embodiment, an MEKK/JNKK-contingent signal transduction pathway can be regulated by administration of a compound which regulates a signal transduction molecule selected from the group of MEKK1, MEKK2, MEKK3, MEKK4, JNKK, JNK1 and JNK2, such that cytokine production is regulated. Preferably, such a compound regulates such a signal transduction molecule by a method such as degrading the molecule, binding an inhibitory compound to the molecule, inhibiting transcription of the molecule, inhibiting translation of the molecule, and inhibiting the interaction of the molecule with another signal transduction molecule.

A preferred embodiment of the present invention relates to a method to regulate cytokine production in a hematopoietic cell expressing FcεRI by regulating an MEKK/JNKK-contingent signal transduction pathway in such cell. Regulation of an MEKK/JNKK-contingent signal transduction pathway can further comprise regulating other signal transduction pathways that affect the MEKK/JNKK-contingent signal transduction pathway.

Another embodiment of the present invention relates to a method to identify compounds which regulate cytokine production in a hematopoietic cell. Such a method comprises contacting a cell with a putative regulatory compound and determining whether such a compound is capable of regulating cytokine production in a cell by regulating an MEKK/JNKK-contingent signal transduction pathway in the cell.

Yet another embodiment of the present invention relates to a kit for identifying compounds which regulate cytokine production by regulating an MEKK/JNKK-contingent signal transduction pathway.

Another embodiment of the present invention relates to a method to treat a disease involving cytokine production in an animal by regulating an MEKK/JNKK-contingent signal transduction pathway. In one embodiment, such a treatment involves administering to an animal an effective amount of a compound which interacts with a signal transduction molecule in an MEKK/JNKK-contingent signal transduction pathway such that cytokine production is regulated.

A preferred embodiment of the present invention relates to a method to treat allergic inflammation by regulating cytokine production. Such regulation of cytokine production is effected by regulation of an MEKK/JNKK-contingent signal transduction pathway.

Yet another embodiment of the present invention relates to a compound for regulating cytokine production. Such a compound interacts with a signal transduction molecule in an MEKK/JNKK-contingent signal transduction pathway in a manner effective to regulate cytokine production.

Another embodiment of the present invention relates to a cell used in a method to identify compounds capable of regulating cytokine production, comprising a cell having at least one heterologous mammalian nucleic acid sequence encoding at least one protein involved in an MEKK/JNKK-contingent signal transduction pathway. A preferred embodiment relates to a method of using such a cell to screen putative regulatory compounds for their ability to regulate cytokine production in said cell.

DETAILED DESCRIPTION OF THE INVENTION

Figure 1:
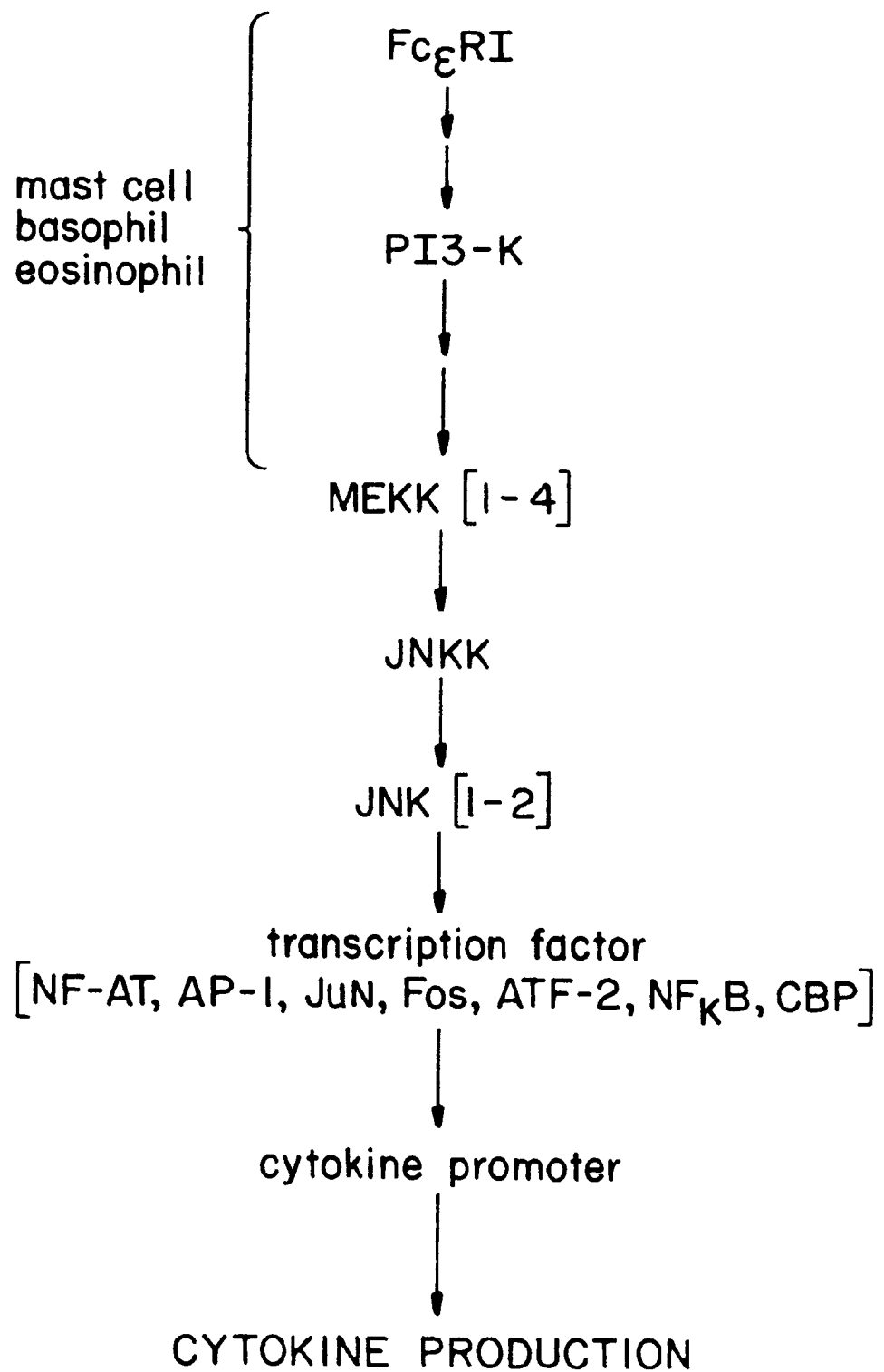
FIG. 1 schematically illustrates an MEKK/JNKK-contingent signal transduction pathway of the present invention.

The present invention relates to the elucidation of a novel signal transduction pathway that regulates cytokine production in hematopoietic cells and a method to target such a pathway to regulate cytokine production by such cells. The regulation of cytokine production in a hematopoietic cell is useful since cytokines are known to play a critical role in the pathogenesis of many diseases. In particular, regulation of cytokine production in a cell expressing FceRI, such as a mast cell, is useful for treating diseases involving allergic inflammation. Specifically, the present invention relates to the regulation of an MEKK/JNKK-contingent signal transduction pathway, in order to regulate cytokine production in a hematopoietic cell.

Prior to the present invention, it was thought that signal transduction through the ERK pathway lead to increases in gene transcription and proliferation, including cytokine gene transcription. Since the ERK pathway is known to be distinct from the pathway of the present invention, the present discovery that an ERK-independent signal transduction pathway regulates cytokine production is unexpected and surprising.

As used herein, the phrase "signal transduction pathway" refers to at least one biochemical reaction, but more commonly a series of biochemical reactions, which result from interaction of a cell with a stimulatory compound. Thus, the interaction of a stimulatory compound with a cell generates a "signal" that is transmitted through the signal transduction pathway, ultimately resulting in a cellular response.

A signal transduction pathway of the present invention can include a variety of signal transduction molecules that play a role in the transmission of a signal from one portion of a cell to another portion of a cell. Signal transduction molecules of the present invention include, for example, cell surface receptors and intracellular signal transduction molecules. As used herein, the phrase "cell surface receptor" includes molecules and complexes of molecules capable of receiving a signal and the transmission of such a signal across the plasma membrane of a cell. An example of a "cell surface receptor" of the present invention is FceRI. As used herein, the phrase "intracellular signal transduction molecule" includes those molecules or complexes of molecules involved in transmitting a signal from the plasma membrane of a cell through the cytoplasm of the cell, and in some instances, into the cell's nucleus. In the present invention, MEKK1, MEKK2, MEKK3, MEKK4, JNKK, JNK1 and JNK2 are "intracellular signal transduction molecules", but can also be referred to as "signal transduction molecules".

A signal transduction pathway in a cell can be initiated by interaction of a cell with a stimulator that is inside or outside of the cell. If an exterior (i.e. outside of the cell) stimulator interacts with a cell surface receptor, a signal transduction pathway can transmit a signal across the cell's membrane, through the cytoplasm of the cell, and in some instances into the nucleus. If an interior (e.g. inside the cell) stimulator interacts with an intracellular signal transduction molecule, a signal transduction pathway can result in transmission of a signal through the cell's cytoplasm, and in some instances into the cell's nucleus.

As used herein, the term "molecule" refers to a protein, a lipid, a nucleic acid or an ion, and at times is used interchangeably with such terms. In particular, a signal transduction molecule refers to a protein, a lipid, a nucleotide, or an ion involved in a signal transduction pathway.

A signal transduction molecule of the present invention can regulate the activity of proteins involved in the transcription of genes involved in cell growth within the nucleus of a cell, in particular, cytokine genes, thereby altering the biological function of a cell.

Signal transduction can occur through: the phosphorylation of a molecule; non-covalent allosteric interactions; complexing of molecules; the conformational change of a molecule; calcium release; inositol phosphate production; proteolytic cleavage; cyclic nucleotide production and diacylglyceride production. Preferably, signal transduction occurs through phosphorylating a signal transduction molecule including, MEKK1, MEKK2, MEKK3, MEKK4, JNKK, JNK1 and JNK2. According to the present invention, all the signal transduction molecules of the MEKK/JNKK-contingent signal transduction pathway need not be known in order to successfully utilize the methods of the present invention.

According to the present invention, an MEKK/JNKK-contingent signal transduction pathway refers generally to a pathway in which MEKK protein regulates a pathway that includes JNKK, molecules which are active between MEKK and JNKK in the pathway, and molecules downstream of JNKK, such as JNK1, JNK2, NF-AT, AP-1, Jun, Fos, ATF-2, NFkB, and CBP. An MEKK/JNKK-contingent signal transduction pathway is independent of an ERK-dependent signal transduction pathway downstream from the effects of MEKK. In other words, the regulation of the MEKK/JNKK-contingent signal transduction pathway does not, of necessity, also affect signal transduction downstream from the ERK protein. A suitable MEKK/JNKK-contingent signal transduction pathway includes a pathway involving an MEKK\JNKK-contingent signal transduction molecule, including MEKK1, MEKK2, MEKK3, MEKK4, JNKK, JNK1 and JNK2, but not ERK molecules exclusively involved in an ERK-dependent signal transduction pathway. More particularly, an MEKK\JNKK-contingent molecule regulates a pathway that is substantially independent of an ERK-dependent pathway if the MEKK/JNKK-contingent protein induces phosphorylation of JNKK or a member of the pathway downstream of JNKK (e.g., proteins including JNK1, JNK2, NF-AT, AP-1, Jun, Fos, ATF-2, NFkB, and/or CBP), and induces cytokine production in a cell having such a pathway. A schematic representation of the proposed signal transduction pathway of the present invention is shown in FIG. 1.

As a result of the elucidation by the present inventors of the novel function of MEKK/JNKK-contingent signal transduction pathway (i.e. regulation of cytokine production), one of skill in the art can determine that regulation of such a pathway by an MEKK/JNKK-contingent molecule is substantially independent of an ERK-pathway. One can also determine how an MEKK/JNKK-contingent molecule regulates the phosphorylation of a downstream member of an MEKK/JNKK-contingent pathway or, alternatively, how to regulate cytokine production in a cell through the inhibition and/or stimulation of the MEKK/JNKK-contingent pathway.

An "ERK-dependent pathway" can refer to a signal transduction pathway in which ERK protein regulates a signal transduction pathway that is substantially independent of an MEKK/JNKK-contingent pathway, or a pathway in which ERK protein regulation converges with common members of a pathway involving MEKK/JNKK-contingent protein. More particularly, an ERK-dependent pathway includes components downstream of ERK proteins and continues downstream in a series of signal transduction events. The independence of regulation of a pathway by an ERK protein from the regulation of a pathway by an MEKK/JNKK-contingent protein can be determined using methods as described above in relation to the MEKK/JNKK-contingent pathway. In particular, regulation of an ERK-dependent pathway will not lead to the regulation of cytokine production in a cell.

As referenced in the present invention, MEKK, or mitogen ERK kinase kinase, is a signal transduction molecule that is capable of phosphorylating mitogen ERK kinase or MAPK kinase (MEK) and/or c-Jun amino-terminal kinase kinase (JNKK), thereby activating such molecules. Several members of the MEKK family have been identified, including MEKK1, MEKK2, MEKK3, and MEKK4. An MEKK molecule of the MEKK/JNKK-contingent signal transduction pathway of the present invention phosphorylates JNKK. In a preferred embodiment, MEKK1 phosphorylates JNKK in response to activation through an FceRI-activated, PI3-kinase-dependent pathway in a mast cell. MEK protein is not a component of the MEKK/JNKK-contingent signal transduction pathway of the present invention.

JNK-activating protein kinase (JNKK), is a dual-specificity threonine-tyrosine protein kinase that activates JNK and functions downstream from MEKK. JNK is a distant member of the mitogen-activated protein kinase superfamily, designated c-Jun amino-terminal kinase (JNK). JNK is activated following dual phosphorylation at a Thr-Pro-Tyr motif in response to diverse stimuli including tumor necrosis factor-α, heat shock, or ultraviolet irradiation. Costimulation of T cells with antibodies to the T cell receptor and CD28 or the stimulation of B cells with anti-CD40 antibody also induces the activation of JNK. JNK functions to phosphorylate c-Jun at the amino-terminal regulatory sites, serine 63 and serine 73, mapping within its transactivation domain. Phosphorylation of these sites in response to UV irradiation also results in the transcriptional activation of c-Jun. There are two members of the JNK family, designated JNK1 and JNK2. It has been suggested that JNK may be involved in apoptosis, but until the present invention, it was not appreciated that JNK was involved in a signal transduction pathway that regulated cytokine production in a cell.

One embodiment of the present invention is directed to a method to regulate cytokine production in a hematopoietic cell, comprising regulating an MEKK/JNKK-contingent signal transduction pathway. In a preferred embodiment, regulation of such a pathway results in inhibition of cytokine production.

As used herein, the term "regulate" can be used interchangeably with the term "modulate". "To regulate" a molecule, a pathway, or a function of such a molecule or pathway, in the present invention refers to specifically controlling, or influencing the activity of such a molecule, pathway, or function, and can include regulation by activation, stimulation, inhibition, alteration or modification of such molecule, pathway or function.

In a preferred embodiment, regulating an MEKK/JNKK-contingent signal transduction pathway comprises regulating a signal transduction molecule selected from the group consisting of MEKK1, MEKK2, MEKK3, MEKK4, JNKK, JNK1, and JNK2. Preferably, regulation of such a signal transduction molecule is accomplished by a method including, but not limited to, degrading said molecule, binding a regulatory compound to said molecule, inhibiting transcription of said molecule, inhibiting translation of said molecule, inhibiting activation of said molecule, and inhibiting the interaction of said molecule with another signal transduction molecule.

In a preferred embodiment of the present invention, an MEKK/JNKK-contingent signal transduction pathway is regulated by administration of an effective amount of a compound that interacts with a signal transduction molecule of said pathway such that cytokine production is regulated. Preferably, such a compound regulates a signal transduction molecule selected from the group of MEKK1, MEKK2, MEKK3, MEKK4, JNKK, JNK1 and JNK2. In another embodiment, such a compound regulates PI3-K. A regulatory compound of the present invention, however, does not regulate a molecule specific to an ERK-dependent pathway. Thus, although in some cell types, for example, PI3-K may regulate other signal transduction pathways in addition to an MEKK/JNKK-contingent pathway, regulation of PI3-K to effect regulation of an MEKK/JNKK-contingent pathway is still within the scope of the present invention.

As used herein, an "effective amount" of a compound is at least the minimum amount of a compound that is necessary to minimally achieve, and more preferably, optimally achieve, the desired effect (i.e. regulation of a signal transduction molecule). An effective amount for use in a given method can be readily determined by one skilled in the art without undue experimentation, depending upon the particular circumstances encountered (e.g. concentrations, cell type and number, etc.).

A regulatory compound of the present invention regulates cytokine production in a hematopoietic cell, comprising a compound that is capable of regulating an MEKK/JNKK-contingent signal transduction pathway of the present invention. Such a regulatory compound includes a compound that is capable of inhibiting an MEKK/JNKK-contingent signal transduction pathway of the present invention, a compound that is capable of stimulating an MEKK/JNKK-contingent signal transduction pathway of the present invention, or a compound that is capable of preventing both the stimulation and the inhibition of the activity of an MEKK/JNKK-contingent signal transduction pathway of the present invention (i.e., maintaining the activity of a signal transduction pathway). Such regulation by a compound can be effected by, but is not limited to, any of the preferred methods of regulating a signal transduction molecule as described above (i.e. degrading a signal transduction molecule, etc.).

Acceptable protocols to contact a cell with a regulatory compound in an effective manner can be accomplished by those skilled in the art based on variables such as, the conditions under which the compound is being administered, the type of cell being regulated and the chemical composition of the regulatory compound (i.e., size, charge etc.) being administered.

As used herein, "inhibiting the interaction of" one molecule with another can be accomplished in a variety of ways including, but not limited to, physically blocking the interaction between two molecules (i.e. by a regulatory compound), moving one molecule relative to the other such that interaction between the two can not occur, dephosphorylating or preventing phosphorylation of one or both molecules such that interaction can not occur, and phosphorylating one or both molecules such that interaction can not occur.

Inhibiting activation of a molecule can be accomplished by a method including, but not limited to, preventing activation of said molecule and deactivating a molecule that is activated. Such methods include, but are not limited to, phosphorylating a molecule, dephosphorylating a molecule, preventing phosphorylation of a molecule, physically inhibiting activation of a molecule as described above, and degrading a molecule.

In one embodiment of the present invention, signal transduction pathways involved in cytokine production in a hematopoietic cell are regulated by a method comprising inhibiting the interactions between molecules selected from a group of MEKK1, MEKK2, MEKK3, MEKK4, JNKK, JNK1 and JNK2, in a hematopoietic cell having an MEKK/JNKK-contingent signal transduction pathway. Such inhibition of interactions between such signal transduction molecules can be effected by methods of regulation described herein, including, but not limited to, contacting a cell with a compound which modulates the interactions between such molecules.

According to the present invention, a hematopoietic cell is a cell which includes erythrocyte cells (i.e., a red blood cell), certain leukocyte cells, including granular leukocytes (eosinophils, basophils, neutrophils, and mast cells), non-granular leukocytes (megakaryocytes, polymorphonuclear cells, lymphocytes and monocytes), or thrombocyte cells (i.e., platelet cell). A preferred hematopoietic cell of the present invention includes a mast cell, a basophil, an eosinophil, a neutrophil, a T cell, a B cell, a macrophage, a dendritic cell, and a natural killer cell.

Cytokine production, as used in the present invention, refers to the de novo synthesis of mRNA encoding such a cytokine which results in the translation and exocytosis of such a cytokine. A cytokine for which production can be regulated in the present invention can be selected from the group consisting of TNF-a, IL-1, IL-2, IL-3, IL-4, IL-5, IL-6, IL-7, IL-8, IL-9, IL-10, IL-11, IL-12, IL-13, IL-14, IL-15, IL-16, G-CSF, GM-CSF, TNF-b, TGF-b, IFN-$\gamma$, and IFN-α/β. It is within the scope of the present invention that cytokines that are unknown at the time of the present invention, but are described in the art in the future, may also be a cytokine that can be regulated by the MEKK/JNKK-contingent pathway of the present invention. In a preferred embodiment, production of TNF-a by a mast cell is regulated. The de novo synthesis of cytokine production is regulated by activation of an MEKK/JNKK-contingent signal transduction pathway of the present invention. In a preferred embodiment, activation of such a pathway results in modulation of the interaction of transcription factors with cytokine promoters which can thereby regulate cytokine production.

A cytokine promoter as described herein can include any DNA sequence capable of being specifically bound by an RNA polymerase in such a manner that the RNA polymerase can unwind the DNA strand to initiate RNA synthesis of a cytokine gene.

A transcription factor of the present invention is capable of mediating the rate of cytokine transcription in a cell. The rate of transcription of a particular cytokine DNA molecule in a cell is not necessarily fixed and can change according to the needs of the cell in different conditions of growth. Such regulation of transcription can be mediated by proteins that, by binding to DNA near or within a promoter, can increase or decrease the rate at which RNA polymerase initiates RNA synthesis. Transcription rates can be mediated by proteins including transcription factors. Suitable transcription factors include, but are not limited to, at least a portion of a transcription factor. A transcription factor as referred to herein has a transactivation domain capable of regulating the activity of the transcription factor. Such a transcriptional activation domain contains amino acid residues capable of being phosphorylated, the phosphorylation of which results in the regulation of the activity of the transcription factor. Without being bound by theory, it is believed that phosphorylation of residues contained in a transcriptional activation domain alters the conformation of the transcription factor such that the DNA binding domain of the transcription complex can drive transcription. Preferred sites of phosphorylation include serine residues and threonine residues spaced in such a manner that the phosphorylation of such residues results in the activation of the transcription factor. Preferred transcription factors of the present invention include NF-AT, Ap-1, Jun, Fos, ATF-2, NFkB, and CBP.

In one embodiment of the present invention, a hematopoietic cell, in which cytokine production is regulated, expresses FceRI. Preferably, cytokine production in such a cell is inhibited by regulation of an MEKK/JNKK-contingent signal transduction pathway. In a preferred embodiment, activation of an MEKK/JNKK-contingent signal transduction pathway is initiated through aggregation of FceRI. FceRI is the high-affinity receptor for IgE. Hematopoietic cells expressing FceRI in the present invention are preferably mast cells, basophils and eosinophils, and most preferably mast cells. The multivalent binding of an antigen to receptor-bound IgE and the subsequent aggregation of the high-affinity Fc receptors for IgE (FceRI) provide the trigger for activation of mast cells. The first demonstrable response to FceRI aggregation is tyrosine phosphorylation and activation of phospholipase Cγ, which catalyzes the hydrolysis of phosphatidylinositol 4,5-bisphosphate resulting in the liberation of inositol 1,4,5-trisphosphate and diacylglycerol. The elevation of diacylglycerol and the mobilization of $Ca^{2+}$ from intracellular and extracellular sources results in the activation of protein kinase c.

The FceRI is composed of three subunits, single α and β chains, and a homodimer of disulfide-linked γ chains. The intracellular tails of the β and γ chains contain a motif that is important for signal transduction. This motif has been called the antigen recognition activation motif or tyrosine activation motif, which is thought to couple the FceRI to protein tyrosine kinases. Activation of protein tyrosine kinases is one of the earliest signaling events induced by aggregation of the FceRI on mast cells. The aggregation of FceRI initiates diverse signal transduction pathways. As is shown for the first time herein, one of these pathways is the MEKK/JNKK-contingent signal transduction pathway which leads to cytokine production.

In a preferred embodiment of the present invention, an MEKK/JNKK-contingent signal transduction pathway is activated through a phosphatidylinositol 3-kinase (PI3-K) signal transduction pathway. More particularly, such a PI3-K signal transduction pathway is activated through aggregation of FceRI on the surface of a mast cell, a basophil, or an eosinophil. As used herein, a PI3-K pathway is a signal transduction pathway that involves the signal transduction molecule, PI3-K. PI3-K is a heterodimeric protein composed of a non-catalytic p85 α subunit (85 kD) and a catalytic p110 β subunit (110 kD). PI3-Kγ is a 110 kD enzyme specifically regulated by G proteins. PI3-K is capable of phosphorylating inositol lipids on the D-3 hydroxyl position. Contained within the p85 subunit are two proline-rich domains. PI3-Kγ is reguled by G protein subunits, particularly βγ subunits.

The present inventors have unexpectedly found that the PI3-K inhibitor, wortmannin, at concentrations that inhibit PI3-kinase activity, also inhibited JNK activation, but not ERK activation. This finding is the first demonstration of a role for PI3-kinase in regulating a JNK pathway by an Src family tyrosine kinase-associated receptor. Thus, in mast cells the regulation of the MEKK1, JNKK, JNK pathway is dependent on the activation of PI3-kinase, which in turn, is activated by aggregation of FceRI. Mechanistically, there is a very early separation in the signal pathways activated by the FceRI to differentially regulate JNK and ERK sequential protein kinase pathways. Without being bound by theory, the present inventors believe that PI3-kinase activity is involved in activating the MEKK/JNKK-contigent pathway in mast cells downstream of tyrosine kinases and upstream of MEKK1.

In a preferred embodiment of the present invention, regulation of cytokine production by regulating an MEKK/JNKK-contingent signal transduction pathway further comprises regulating PI3-kinase.

Such regulation can be effected by the methods described herein for regulation of an MEKK/JNKK-contingent signal transduction molecule, and/or by interfering with the capability of PI3-K to trigger downstream signal transduction events. In yet another preferred embodiment of the present invention, a method to regulate cytokine production in a cell further comprises regulating a signal transduction pathway selected from the group of a c-kit signal transduction pathway and a p38 signal transduction pathway. The c-kit and the p38 signal transduction pathways are distinct from the MEKK/JNKK-contingent signal transduction pathway of the present invention. It is appreciated for the first time in the present invention, that both the c-kit and the p38 signal transduction pathways can enhance the regulation of cytokine production that is effected by the MEKK/JNKK-contingent signal transduction pathway. c-kit is a cell-surface receptor that, when bound by c-kit ligand, initiates a signal transduction pathway that is incapable of regulating cytokine production itself, but that can enhance the effects of the MEKK/JNKK-contingent pathway on cytokine production. p38 is activated by dual phosphorylation at a Thr-Gly- Tyr motif and is activated by cellular stress, pro-inflammatory cytokines, and lipopolysaccharide (LPS). p38 can be activated by a specific JNKK referred to as MKK3 or MKK6; however, in the MEKK/JNKK-contingent signal transduction pathway of the present invention, JNK is preferentially activated over p38. Therefore, signal transduction through the MEKK/JNKK-contingent signal transduction pathway is primarily responsible for regulation of cytokine production in a cell, but can be enhanced by other signal transduction pathways. Regulation of such other pathways can be effected by the methods described herein for regulation of an MEKK/JNKK-contingent signal transduction pathway.

One aspect of the present invention includes a method to identify compounds that regulate an MEKK/JNKK-contingent signal transduction pathway. Such compounds are referred to herein as "putative regulatory compounds". As used herein, the term "putative" refers to compounds having an unknown signal transduction regulatory activity, at least with respect to the ability of such compounds to regulate cytokine production via the MEKK/JNKK-contingent pathway. Regulatory compounds, defined by their identifying characteristics of being capable of regulating signal transduction molecules of the present invention have been previously described herein.

Putative regulatory compounds as referred to herein include, for example, compounds that are products of rational drug design, natural products and compounds having partially defined signal transduction regulatory properties. A putative compound can be a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof. A putative regulatory compound can be obtained, for example, from libraries of natural or synthetic compounds, in particular from chemical or combinatorial libraries (i.e., libraries of compounds that differ in sequence or size but that have the same building blocks) or by rational drug design.

A method to identify a regulatory compound of the present invention comprises the steps of providing a hematopoietic cell having an MEKK/JNKK-contingent signal transduction pathway, contacting such a cell with a putative regulatory compound, and determining whether such a compound is capable of regulating said MEKK/JNKK-contingent signal transduction pathway. In a preferred embodiment, such a method is used to identify a regulatory compound that inhibits cytokine production by said cell.

In particular, a preferred regulatory compound of the present invention can be identified by determining the ability of such a compound to modulate the interactions between signal transduction molecules selected from the group of MEKK1, MEKK2, MEKK3, MEKK4, JNKK, JNK1, and JNK2. More preferably, the regulation of such a signal transduction molecule by a regulatory compound of the present invention modulates the interaction of such a molecule with a transcription factor selected from the group of NF-AT, Ap-1, Jun, Fos, ATF-2, NFkB and CBP. In another preferred embodiment, a regulatory compound is identified by its ability to modulate the interaction of PI3-K with signal transduction molecules in the MEKK/JNKK-contingent pathway.

Another embodiment of the present invention is a kit for identifying compounds capable of regulating cytokine production in a hematopoietic cell. Such a kit comprises a hematopoietic cell capable of producing an amount of at least one cytokine, such cell having an MEKK/JNKK-contingent signal transduction pathway, and production of such cytokine being dependent on such MEKK/JNKK-contingent signal transduction pathway. Such a kit further comprises a means for determining a change in said amount of cytokine produced by such a cell after the cell is contacted with a putative regulatory compound. In a preferred embodiment, such a kit is useful for identifying compounds that inhibit cytokine production by said cell.

As used herein, "at least one cytokine" means that a minimum of one cytokine selected from the group of TNF-a, IL-1, IL-2, IL-3, IL-4, IL-5, IL-6, IL-7, IL-8, IL-9, IL-10, IL-11, IL-12, IL-13, IL-14, IL-15, IL-16, G-CSF, GM-CSF, TNF-b, TGF-b, IFN-$\gamma$, and IFN-$\alpha/\beta$., can be produced by a cell of the kit of the present invention. It is within the scope of the present invention that more than one cytokine can be produced by such a cell. As used herein, "an amount" of a cytokine refers to a quantity of cytokine produced by a hematopoietic cell that is detectable by standard methods of cytokine measurement in the art. "An amount" can refer to a detectable protein concentration of cytokine in a sample, or to units of activity of such a cytokine in a sample. "A change in the amount" of cytokine produced by a hematopoietic cell after such a cell is contacted by a putative regulatory compound, is any detectable change, (i.e. increase or decrease) in the amount of cytokine produced by such a cell after contact with such a regulatory compound, as compared to the amount of cytokine produced before such cell was contacted with such a compound.

Suitable cells for use with either the method to detect a regulatory compound or with the kit useful for detecting a regulatory compound of the present invention include any cell that has an MEKK/JNKK-contingent signal transduction pathway. Such cells can include normal cells or transformed derivatives thereof, that express a receptor in a native physiological context (e.g., basophils, eosinophils, neutrophils, monocytes, macrophages, and lymphoid cells). Alternatively, cells for use with the present invention can include spontaneously occurring variants of normal cells, or genetically engineered cells, that have altered signal transduction activity, such as enhanced responses to particular ligands. Signal transduction variants of normal cells can be identified using methods known to those in the art. For example, variants can be selected using fluorescence activated cell sorting (FACS) based on the level of calcium mobilization by a cell in response to a ligand. Genetically engineered cells can include recombinant cells of the present invention (described in detail below) that have been transformed with, for example, a recombinant molecule encoding a signal transduction molecule and/or a transcription indicator recombinant molecule of the present invention.

Cells for use with the present invention include mammalian, invertebrate, plant, insect, fungal, yeast and bacterial cells. Preferred cells include mammalian, amphibian and yeast cells. Preferred mammalian cells include primate, mouse and rat cells. In a preferred embodiment, cells to be used in a method to identify compounds which regulate an MEKK/JNKK-contingent signal transduction pathway can be genetically manipulated to obtain cells having an MEKK/JNKK-contingent signal transduction pathways wherein production of cytokines by such cells is dependent on the MEKK/JNKK-contingent signal transduction pathway and/or components of such signal transduction pathway. In a preferred embodiment, such cells are substantially devoid of any other signal transduction pathways that result in significant production of cytokines by such cell.

In yet another embodiment, a cell suitable for use in the present invention further comprises a PI3-K signal transduction pathway which activates said MEKK/JNKK-contingent pathway, and/or a p38 signal transduction pathway or a c-kit signal transduction pathway which enhances said MEKK/JNKK-contingent pathway.

In one embodiment, a cell suitable for use in the present invention has at least one type of cell surface receptor. A cell surface receptor as referred to herein includes those cell surface receptors capable of binding to a ligand (as described in detail below) and capable of initiating an MEKK/JNKK-contingent signal transduction pathway in a cell upon ligand binding. A cell surface receptor typically includes an external portion located on the outer surface of a plasma membrane of a cell, a transmembrane portion that spans the plasma membrane, and a cytoplasmic portion located on the inner surface of the plasma membrane.

A cell surface receptor as described herein can be produced by expression of a naturally occurring gene encoding a cell surface receptor and/or a heterologous nucleic acid molecule transformed into a cell. An example of a cell surface receptor of the present invention could be, for example, CD40, CD28, or FceRI. A preferred cell surface receptor of the present invention is FceRI.

An intracellular signal transduction molecule as described herein can be produced in a cell by expression of a naturally occurring gene and/or by expression of a heterologous nucleic acid molecule transformed into the cell. Preferred intracellular signal transduction molecules of the present invention are MEKK1, MEKK2, MEKK3, MEKK4, JNKK, JNK1 and JNK2. MAPK/ERK molecules are not intracellular signal molecules of the present invention.

In certain embodiments, a cell of the present invention is transformed with at least one heterologous nucleic acid sequence. A nucleic acid sequence, or molecule, as described herein can be DNA, RNA, or hybrids or derivatives of either DNA or RNA. Nucleic acid molecules as referred to herein can include regulatory regions that control expression of the nucleic acid molecule (e.g., transcription or translation control regions), full-length or partial coding regions, and combinations thereof. It is to be understood that any portion of a nucleic acid molecule can be produced by: (1) isolating the molecule from its natural milieu; (2) using recombinant DNA technology (e.g., PCR amplification, cloning); or (3) using chemical synthesis methods. A gene includes all nucleic acid sequences related to a natural cell surface receptor gene such as regulatory regions that control production of a cell surface receptor encoded by that gene (such as, but not limited to, transcription, translation or post-translation control regions) as well as the coding region itself.

A nucleic acid molecule can include functional equivalents of natural nucleic acid molecules encoding a protein or functional equivalents of natural nucleic acid sequences capable of being bound by proteins. Functional equivalents of natural nucleic acid molecules can include, but are not limited to, natural allelic variants and modified nucleic acid molecules in which nucleotides have been inserted, deleted, substituted, and/or inverted in such molecules without adversely affecting the function of products encoded by such sequences.

As guidance in determining what particular modifications can be made to any particular nucleic acid molecule, one of skill in the art should consider several factors that, without the need for undue experimentation, permit a skilled artisan to appreciate workable embodiments of the present invention. For example, such factors include modifications to nucleic acid molecules done in a manner so as to maintain particular functional regions of the encoded proteins including, a ligand binding site, a target binding site, a catalytic domain, etc. Functional tests for these various characteristics (e.g., ligand binding studies and signal transduction assays such as kinase assays, transcription assays, and other assays described in detail herein) allows one of skill in the art to determine what modifications to nucleic acid sequences would be appropriate and which would not.

Transformation of a heterologous nucleic acid molecule (e.g., a heterologous cell surface receptor encoding nucleic acid molecule) into a cell suitable for use in the present invention can be accomplished by any method by which a gene is inserted into a cell. Transformation techniques include, but are not limited to, transfection, retroviral infection, electroporation, lipofection, bacterial transfer and spheroplast fusion. Nucleic acid molecules transformed into cells suitable for use in the present invention can either remain on extra-chromosomal vectors or can be integrated into the cell genome.

Expression of a nucleic acid molecule of the present invention in a cell can be accomplished using techniques known to those skilled in the art. Briefly, the nucleic acid molecule is inserted into an expression vector in such a manner that the nucleic acid molecule is operatively joined to a transcription control sequence in order to be capable of affecting either constitutive or regulated expression of the gene when the gene is transformed into a host cell. The phrase "recombinant molecule", as used herein refers to a gene operatively linked to at least one transcription control sequence on an expression vector. The phrase "expression vector", as used herein refers to a DNA or RNA vector that is capable of transforming a host cell, of replicating within the host cell, and of affecting expression of the operatively linked gene. Expression vectors are capable of replicating to either a high or low copy number depending on their inherent characteristics. Transcription control sequences, which can control the amount of protein produced, include sequences that control the initiation, elongation, and termination of transcription. Particularly important transcription control sequences are those which control transcription initiation, such as promoter and upstream activation sequences.

Construction of desired expression vectors can be performed by methods known to those skilled in the art and expression can be in eukaryotic or prokaryotic systems. Procaryotic systems typically used are bacterial strains including, but not limited to various strains of E. coli, various strains of bacilli or various species of Pseudomonas. In prokaryotic systems, plasmids are used that contain replication sites and control sequences derived from a species compatible with a host cell. Control sequences can include, but are not limited to promoters, operators, enhancers, ribosome binding sites, and Shine-Dalgarno sequences. Expression systems useful in eukaryotic host cells comprise promoters derived from appropriate eukaryotic genes. Useful mammalian promoters include early and late promoters from SV40; other viral promoters such as those derived from baculovirus, polyoma virus, adenovirus, bovine papilloma virus, avian sarcoma virus or cytomegalovirus; or collagenase promoters. Expression vectors include any vectors that function (i.e., direct gene expression) in recombinant cells of the present invention including bacterial, yeast, other fungal, insect, and mammalian cells. Particularly preferred expression vectors include promoters useful for expressing recombinant molecules in human cells.

An expression system can be constructed from any of the foregoing control elements operatively linked to nucleic acid sequences using methods known to those of skill in the art. (see, for example, Sambrook et al., ibid.).

The conditions under which the cell of the present invention is contacted with, such as by mixing, a putative regulatory compound are conditions in which the cell can transduce a normal signal if essentially no regulatory compound is present. Such methods are within the skill in the art, and include an effective medium in which the cell can be cultured such that the cell can exhibit signal transduction activity. A preferred number of cells to use in the method or test kit of the present invention includes a number of cells that enables one to detect a change in activity of a signal transduction molecule using a detection method of the present invention (described in detail below).

In another embodiment of the present invention, cells suitable for use in the present invention are stimulated with ligands capable of binding to cell surface receptors of the present invention to initiate an MEKK/JNKK-contingent signal transduction pathway and thereby regulate cytokine production. Suitable ligands can include, for example, hormones, growth factors, antigens, peptides, ions, other differentiation agents and other cell type specific mitogens. Preferred ligands include IgE, anti-FceRI, and c-kit ligand.

In another embodiment of the present invention, cells suitable for use in the present invention are stimulated with intracellular initiator molecules capable of initiating a signal transduction pathway from inside a cell. Examples of intracellular initiator molecules as referred to herein include, but are not limited to, phorbol esters, calcium ionophores, ALF4, phenyloxide, mastoparans, sodium orthovanadate, arachidonic acid and ceramides.

A suitable amount of putative regulatory compound(s) suspended in culture medium is added to the cells that is sufficient to regulate the activity of a signal transduction molecule inside the cell such that the regulation is detectable using a detection method of the present invention. A preferred amount of putative regulatory compound(s) comprises between about 1 nM to about 10 mM of putative regulatory compound(s) per well of a 96-well plate. The cells are allowed to incubate for a suitable length of time to allow the putative regulatory compound to enter a cell and interact with a signal transduction molecule. A preferred incubation time is between about 1 minute to about 12 hours.

In one embodiment, the method and kit of the present invention include determining if a putative regulatory compound is capable of regulating an MEKK/JNKK-contingent signal transduction pathway by regulating cytokine production in a cell. Such methods of determining a change in an amount of a cytokine after contact of a putative regulatory compound with a cell include: immunoassays for cytokine production, such as by enzyme-linked immunoassay (e.g., ELISA), radioimmunoassay analysis, fluorescence immunoassay or immunoblot assay (as generally described in Sambrook et al., ibid.); transcription assays to detect the activation of cytokine transcription, such as measuring the increase or decrease in mRNA transcription of a cytokine gene by PCR-based technology; and biological assays in which a cytokine-indicator cell is used to determine a change in an amount of cytokine (such cells are known in the art for a large number of cytokines). Particularly useful assays are antibody-based capture assays that comprise: (1) attaching a capture antibody having specificity for a specific cytokine to a support, such as an ELISA plate; (2) contacting a cell supernate with the substrate-bound antibody to form an immune complex; (3) contacting the substrate-bound immune complex with a detection antibody specific for an epitope on the cytokine; and (4) detecting the association of the detection antibody to the immune complex.

It is within the scope of the present invention to determine regulation of an MEKK/JNKK-contingent signal transduction pathway by measuring the activation of signal transduction molecules selected from the group of MEKK1, MEKK2, MEKK3, MEKK4, JNKK, JNK1 and JNK2, by methods such as: kinase assays to detect the phosphorylation of such signal transduction molecules, calcium mobilization assays to detect increases in calcium levels in a cell's cytoplasm, and immunoassays such as those listed above. Such methods are known in the art. The methods of the present invention can further include the step of performing a toxicity test to determine the toxicity of a putative regulatory compound.

One embodiment of the present invention relates to a method to treat a disease involving cytokine production in an animal, comprising regulating an MEKK/JNKK-contingent signal transduction pathway to affect cytokine production by a hematopoietic cell. Such diseases include medical disorders and diseases in which the pathogenesis of the disease and/or the physiological effects of the disease might be ameliorated by regulation of cytokine production. Such diseases include, but are not limited to, allergic diseases, anaphylaxis, diseases involving defects in hematopoietic cells, inflammation, mast cell disorders, sepsis and cancer. According to the present invention, the term treatment can refer to the regulation of the progression of a disease or the complete removal of a disease (e.g., cure).

The present invention preferably relates to a method to treat allergic inflammation, comprising regulating cytokine production in a hematopoietic cell in an animal by regulating an MEKK/JNKK-contingent signal transduction pathway. In one embodiment, such a hematopoietic cell is selected from a group of a mast cell, a basophil and an eosinophil, such a cell expressing FceRI.

In a preferred embodiment, a disease involving cytokine production can be treated by administering to an animal an effective amount of a compound which interacts with a signal transduction molecule in an MEKK/JNKK-contingent signal transduction pathway in a hematopoietic cell of said animal, such that cytokine production by such a cell is regulated. In a preferred embodiment, cytokine production is inhibited.

Signal transduction molecules of an MEKK/JNKK-contingent signal transduction pathway that can be regulated by administration of a regulatory compound include MEKK1, MEKK2, MEKK3, MEKK4, JNKK, JNK1 and JNK2. A preferred compound to administer to an animal to regulate cytokine production by a hematopoietic cell is a compound selected from the group of an MEKK inhibitor, a JNKK inhibitor, and a JNK inhibitor. In a preferred embodiment, a disease involving cytokine production by a hematopoietic cell of an animal can be regulated by administering an effective amount of a compound which inhibits PI3-K.

As used herein, an "inhibitor" of a particular signal transduction molecule inhibits, prevents, decreases, or impedes, the normal activity of such a molecule. An inhibitor can inhibit a specific signal transduction molecule by a means including, but not limited to: causing such a molecule to be degraded, binding to such a molecule such that the molecule is incapable of being activated, binding to such a molecule such that the molecule is unable to interact with other signal transduction molecules, inhibiting transcription of such a molecule, and inhibiting translation of such a molecule.

As used herein, "an effective amount" of such a compound is an amount, or dose, of a regulatory compound, that when administered to an animal, is capable of regulating cytokine production by a hematopoietic cell in said animal.

Effective doses to administer to an animal include doses administered over time that are capable of regulating cytokine production by a hematopoietic cell in the animal. For example, a first effective dose can comprise an amount of a regulatory compound of the present invention that causes a minimal change in cytokine production by a hematopoietic cell when administered to an animal. A second effective dose can comprise a greater amount of the same compound than the first dose. Effective doses can comprise increasing concentrations of the compound necessary to regulate cytokine production and ameliorate a disease involving such cytokine production in an animal such that the animal does not have an immune response to subsequent exposure to the compound. A suitable single dose of a regulatory compound of the present invention is a dose that is capable of substantially regulating cytokine production by a hematopoietic cell when administered one or more times over a suitable time period. A preferred single dose of a regulatory compound ranges from about 0.01 μg to about 1,000 milligrams (mg) of such a compound per subject, more preferred ranges being from about 0.1 μg to about 100 mg of a compound per subject, and even more preferred ranges being from about 1 μg to about 10 mg of a compound per subject.

A regulatory compound of the present invention can be administered to any animal, preferably to mammals, and even more preferably to humans. Acceptable protocols to administer a regulatory compound of the present invention in an effective manner include individual dose size, number of doses, frequency of dose administration, and mode of administration. Determination of such protocols can be accomplished by those skilled in the art depending upon a variety of variables, including the animal to be treated and the stage of disease. Modes of delivery can include any method compatible with prophylactic or treatment of a disease. Modes of delivery include, but are not limited to, parenteral, oral, intravenous, topical administration, local administration, and ex vivo administration to isolated hematopoietic cells.

The following experimental results are provided for purposes of illustration and are not intended to limit the scope of the invention.

EXAMPLES

For the following Examples 1–12, the materials and methods used herein are the same throughout the examples and are therefore described in detail only upon the first appearance of such material or method.

Example 1

The following example demonstrates that JNK is activated through aggregation of FcεRI by antigen or anti-IgE in MC/9 cells.

MC/9, a mouse mast cell line, was originally derived from fetal liver cells cultured in concanavalin A-conditioned medium followed by culture with irradiated syngeneic bone marrow cells. The MC/9 mast cell line was identified as a source of mast cells by light microscopy and the appearance of metachromatic granules. Further characterization includes the findings on electron microscopy and the ability to release histamine upon stimulation with A23187 or with antigen following passive sensitization with IgE. MC/9 cells express FcεRI on the cell surface.

The MC/9 murine mast cell clone was obtained from the American Type Culture Collection (Rockville, Md.) and maintained in Dulbecco's modified Eagle's medium (Life Technologies, Inc.) supplemented with $5 \times 10^{-5}$ M 2-mercaptoethanol (Life Technologies, Inc.), 10% fetal bovine serum (Summit Biotechnology, Ft. Collins, Colo.), and 5% conditioned medium (rat growth factor obtained from Collaborative Biomedical (Bedford, Mass.)). Purified rat anti-mouse IgE monoclonal antibody (R35-72) was purchased from Pharmingen (San Diego, Calif.). Ovalbumin (OVA, grade V) was obtained from Sigma. Recombinant protein G-Sepharose 4B was purchased from Zymed Laboratories (San Francisco, Calif.). An anti-OVA IgE antibody-secreting hybridoma cell line was generated as described. A hybridoma cell line producing monoclonal mouse IgE-specific for 2,4,6-trinitrophenol (TNP), IGEL b4 was purchased from ATCC.

MC/9 cells ($5 \times 10^6$/ml) were cultured with 500 ng/ml anti-OVA IgE for 2 h. The cells were washed with medium three times and cultured with fresh medium for an additional 2 h. OVA dissolved in PBS or anti-IgE was added for the stimulation, and PBS was used as a control vehicle.

The activity of JNK was measured by monitoring the activity of a Glutathione S-transferase-c-Jun-(1-79) fusion protein. Cells ($3 \times 10^6$) were lysed in a buffer (20 mM Tris-HCl, pH 7.6, 250 mM NaCl, 3 mM EDTA, 3 mM EGTA, 0.5% NP-40, 2 mM $Na_3VO_4$, 1 mM dithiothreitol (DTT), 1 mM phenylmethylsulfonyl fluoride (PMSF), 20 μg/ml aprotinin, 5 μg/ml leupeptin). The lysates were mixed with GST-c-Jun-Sepharose beads and rotated at 4° C. for 3 h. The beads were washed twice in lysis buffer and once in kinase assay buffer (20 mM Hepes, pH 7.5, 20 mM β-glycerophosphate, 10 mM $MgCl_2$, 1 mM DTT, 50 mM $Na_3VO_4$, 10 mM p-nitrophenyl phosphate). After the final wash, 40 μl of a kinase assay buffer containing 10 μCi of γ-$^{32}$P-ATP (ICN Pharmaceuticals, Irvine, Calif.) were added per sample. The sample was incubated for 20 min at 30° C. and the reaction was stopped by addition of 13 μl of 4X protein loading buffer (188 mM Tris (pH 6.8), 30% glycerol, 6% sodium dodecyl sulfate (SDS), 15% 2-mercaptoethanol, 0.4% bromophenol blue). The samples were boiled for 3 min, and GST-c-Jun was separated by SDS-12% polyacrylamide gel. The gel was stained with Coomassie brilliant blue, exhaustively destained, dried, and subjected to autoradiography. The bands corresponding to GST-c-Jun were cut out of the gel, and radioactivity was determined by liquid scintillation counting.

Figure 2A:
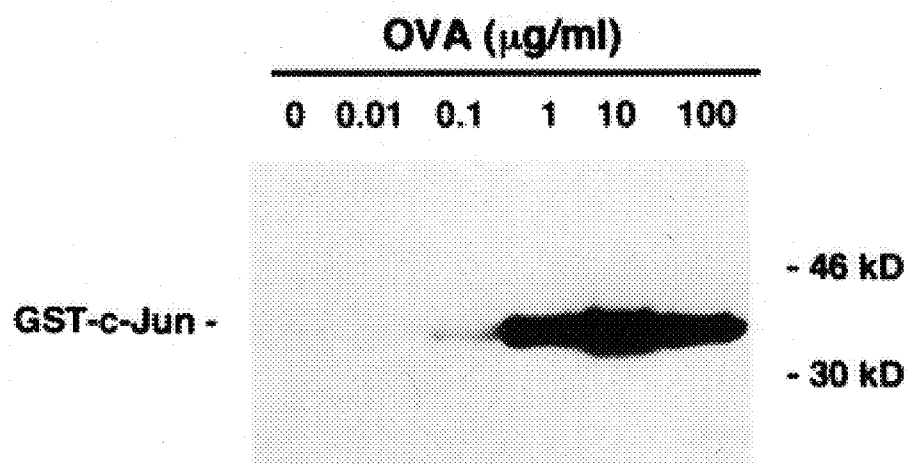
FIG. 2A demonstrates activation of JNK by OVA and OVA-IgE in passively sensitized mast cells.

MC/9 cells were incubated with 500 ng/ml mouse monoclonal IgE specific for OVA (OVA-IgE) for 2 h. After washing, sensitized MC/9 cells were incubated in the presence of 10 ng/ml to 100 g/ml OVA for 10 min. Following addition of OVA to MC/9 cells sensitized with OVA-specific IgE (OVA-IgE), JNK was significantly activated in a dose-dependent manner. 10 μg/ml OVA induced maximal activation of JNK (FIG. 2A).

Figure 2B:
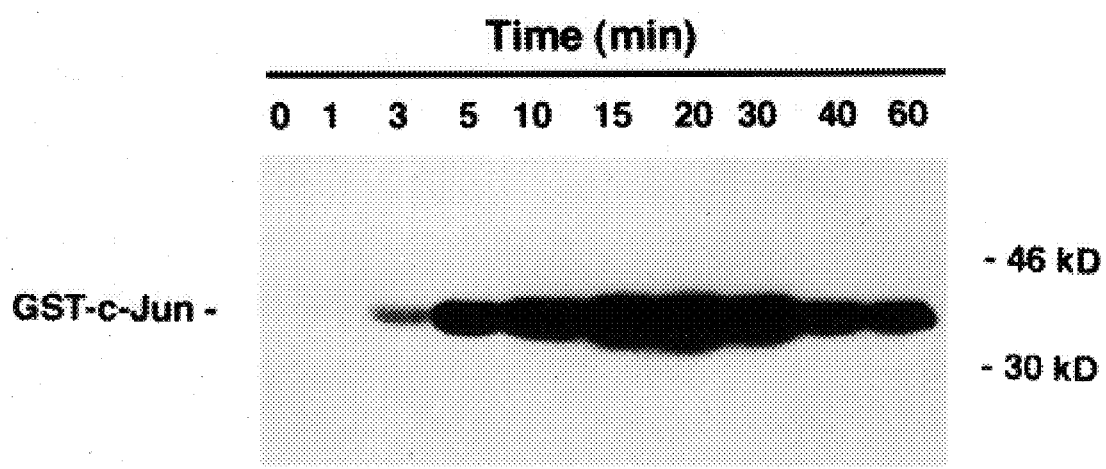
FIG. 2B shows an immunoblot demonstrating JNK activity measured in passively sensitized mast cells over time.
Figure 2C:
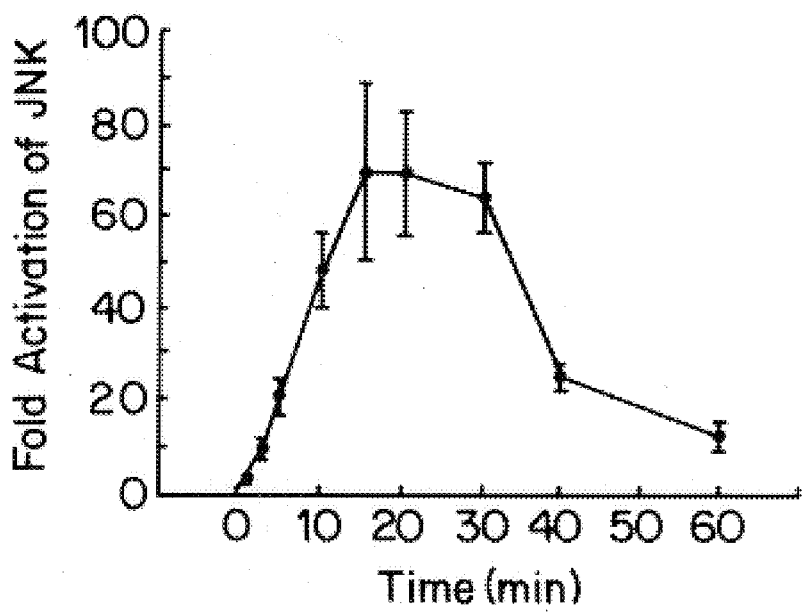
FIG. 2C graphically shows fold-increases in JNK activity in passively sensitized mast cells.

MC/9 cells sensitized with OVA-IgE were incubated in the presence of PBS (0 min) or 10 μg/ml OVA for 1, 3, 5, 10, 15, 20, 30, 40, or 60 min. FIGS. 2B and 2C show representative autoradiography from four independent experiments (2B) and fold increases in JNK activity (mean±S.D., n=4) (2C). JNK was significantly activated within 5 min, and its activation was maximal at 15–20 min after the addition of OVA (FIG. 2B and 2C).

Figure 2D:
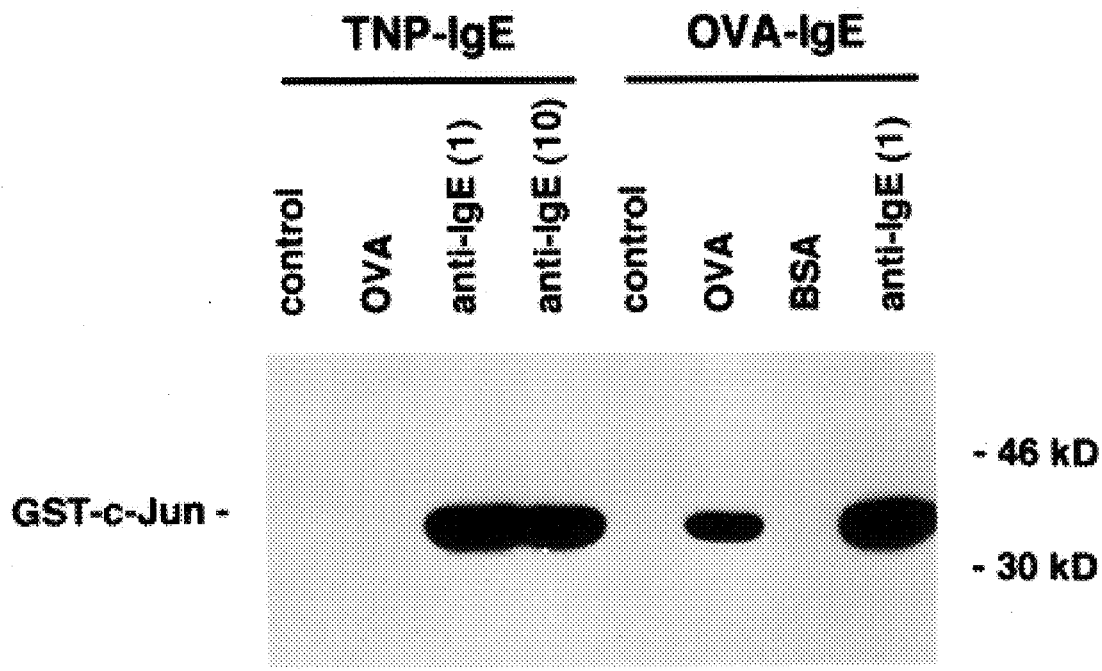
FIG. 2D shows an immunoblot demonstrating the antigen-specificity of JNK activation in passively sensitized mast cells.

MC/9 cells were incubated with 500 ng/ml mouse monoclonal IgE specific for TNP (TNP-IgE) or 500 ng/ml OVA-IgE for 2 h. FIG. 2D shows MC/9 cells sensitized with TNP-IgE were incubated together with PBS (control), 10 μg/ml OVA (OVA), 1 μg/ml rat anti-mouse IgE monoclonal antibody (anti-IgE (1)), or 10 μg/ml anti-mouse IgE (anti-IgE (10)) for 10 min. MC/9 cells sensitized with OVA-IgE were incubated with PBS (control), 10 μg/ml OVA (OVA), 10 μg/ml BSA (BSA), or 1 μg/ml anti-IgE (anti-IgE (1)) for 10 min. GST, glutathione S-transferase. JNK activation by OVA was not induced in MC/9 cells sensitized with TNP-specific IgE (TNP-IgE) and BSA did not activate JNK in MC/9 cells sensitized with OVA-IgE. Anti-mouse IgE antibody activated JNK in both TNP-IgE and OVA-IgE-sensitized cells (FIG. 2D). Student's t test, Welch's t test, or a paired t test was used for the statistical analysis.

Example 2

The following example demonstrates that MEKK1 is activated by antigen in MC/9 cells.

Affinity-purified rabbit polyclonal anti-mouse MEK kinase 1 (MEKK1) antibody was prepared by immunizing rabbits with a recombinant fragment of the amino-terminal domain of MEKK1.

Addition of OVA (10 μg/ml) induced MEKK1 activation in MC/9 cells sensitized with OVA-IgE. As a positive control in the kinase assay for MEKK1, cell lysates from Cos cells that transiently overexpressed full-length MEKK1 were used.

To assay for MEKK1, MEKK1 was first immunoprecipitated by lysing $5 \times 10^6$ cells by vigorous mixing in 0.4 ml of extraction buffer (1% Triton X-100, 10 mM Tris-HCl (pH 7.4), 5 mM EDTA, 50 mM NaCl, 50 mM NaF, 0.1% bovine serum albumin (BSA), 20 μg/ml aprotinin, 1 mM phenylmethylsulfonyl fluoride, and 2 mM $Na_3VO_4$). The lysate was incubated with the affinity-purified rabbit anti-MEKK1 antibody (1:100 dilution) for 2 h at 4° C. Recombinant protein G-Sepharose 4B was added to the lysate and incubated for an additional 30 min at 4° C. The immune complexes were washed twice with radioimmunoprecipitation assay buffer (10 mM sodium phosphate (pH 7.0), 150 mM NaCl, 2 mM EDTA, 1% Nonidet P-40 (Nonidet P-40), 0.1% SDS, 10 μg/ml aprotinin, 1 mM phenylmethylsulfonyl fluoride, 0.1% 2-mercaptoethanol, 50 mM NaF, and 200 μM $Na_3VO_4$), twice with PAN buffer (10 mM PIPES pH 7.0), 100 mM NaCl, 20 μg/ml aprotinin) containing 0.5% Nonidet P-40 and once with PAN. For the in vitro kinase assay, the PAN immune complex suspension was incubated with catalytically inactive JNKK (JNKK-KR) and 30 μCi of [γ-$^{32}$P] ATP in 1×universal kinase buffer (20 mM PIPES (pH 7.0), 10 mM $MnCl_2$, and 20 μg/ml aprotinin) in a final volume of 40 μl for 30 min at 30° C. MEKK1 was transiently expressed in Cos cells by using lipofectamine (Life Technologies, Inc.), and the cell lysate was used as a positive control in the MEKK1 kinase assay. The kinase reaction was terminated by the addition of 4×protein loading buffer, and the mixture was boiled for 5 min, separated by SDS-10% polyacrylamide gel, and transferred to nitrocellulose for autoradiography and immunoblotting. The kinase activity was quantified with a PhosphorImager (Molecular Dynamics, Sunnyvale, Calif.). The membranes were probed using the same anti-MEKK1 antibody with an alkaline phosphatase visualization system (Promega protoblot alkaline phosphatase system, Madison, Wis.).

Figure 3A:
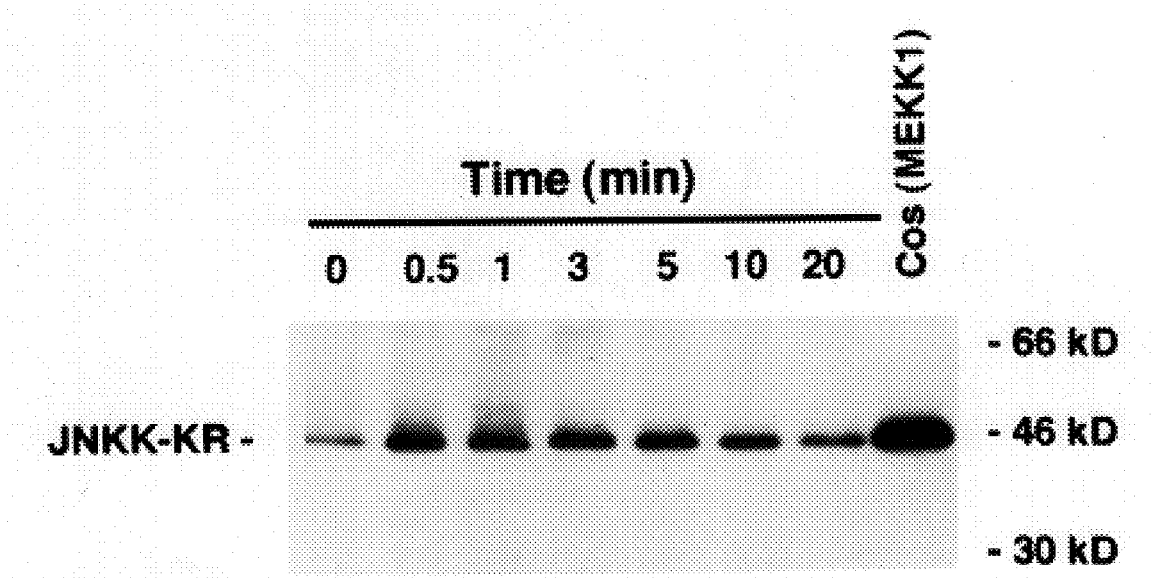
FIG. 3A shows an immunoblot demonstrating the activation of MEKK1 by antigen in passively sensitized mast cells.
Figure 3B:
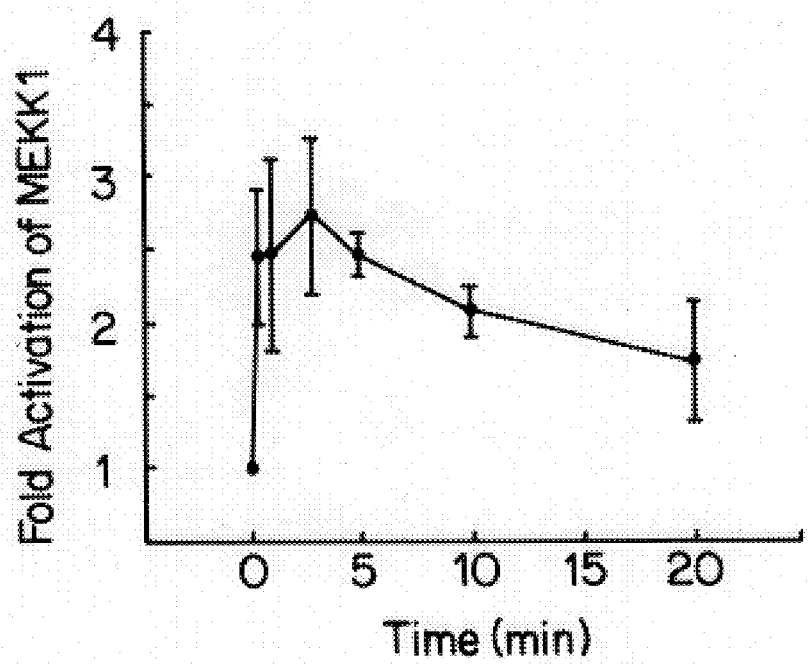
FIG. 3B graphically shows fold-increases in MEKK1 activation by antigen in passively sensitized mast cells.

MC/9 cells sensitized with OVA-IgE were incubated together with PBS (0 min) or 10 μg/ml OVA for 0.5, 1, 3, 5, 10, or 20 min. The cell lysate from Cos cells which expressed full-length MEKK1 (Cos (MEKK1)) was used as a positive control in the kinase assay. MEKK1 activation in MC/9 cells was observed 30 s after the addition of OVA to IgE-sensitized cells. MEKK1 activity reached maximal levels 3 min after OVA addition. MEKK1 activity was increased to 2.5–3-fold over basal activity. FIG. 3A and 3B show a representative autoradiograph from three independent experiments (FIG. 3A) and fold increases in MEKK1 activity (mean±S.E., n=3) (FIG. 3B). Kinase activities decreased gradually by 10 min after addition of OVA. The same membrane in the kinase assay was probed with the anti-MEKK1 antibody used for immunoprecipitation, and reactivity was visualized by the alkaline phosphatase system to ensure that the same amounts of MEKK1 were present in each sample. Immunoblotting showed a 98-kDa bank of MEKK1, and the density in each sample was comparable (data not shown).

Example 3

The following example demonstrates that ERK2 is phosphorylated and activated by antigen ligation in MC/9 cells.

The mouse monoclonal anti-mouse ERK2 antibody and bovine myelin basic protein were obtained from Upstate Biotechnology (Lake Placid, N.Y.). Goat affinity-purified polyclonal anti-ERK2 (C-14, amino acids 345–358) antibody was purchased from Santa Cruz Biotechnology (Santa Cruz, Calif.).

ERK2 activation induced by tyrosine-threonine phosphorylation was observed in immunoblots using anti-ERK2 antibody. After different treatments, $1 \times 10^6$ cells were lysed in buffer (150 mM NaCl, 1% Nonidet P-40, 0.5% deoxycholic acid sodium salt, 0.1% SDS, 50 mM Tris (pH 7.6), 10 μg/ml aprotinin, 5 mg/ml leupeptin, 1 mM phenylmethylsulfonyl fluoride). Samples were electrophoresed on SDS-10% polyacrylamide gels and proteins were transferred to nitrocellulose membranes. Membranes were incubated overnight in blocking buffer containing 1% BSA at 4° C. The monoclonal anti-ERK2 antibody (200 μg/69 μl, Upstate Biotechnology) was added to the blocking buffer (1:1000), and blots were incubated for an additional 1 h at room temperature. The blots were washed in TBST (25 mM Tris (pH 8.0), 125 mM NaCl, 0.025% Tween 20), and specific reactive proteins were detected by an enhanced chemiluminescence method, employing a sheep anti-mouse Ig antibody linked to horseradish peroxidase (Amersham Corp.).

Figure 4A:
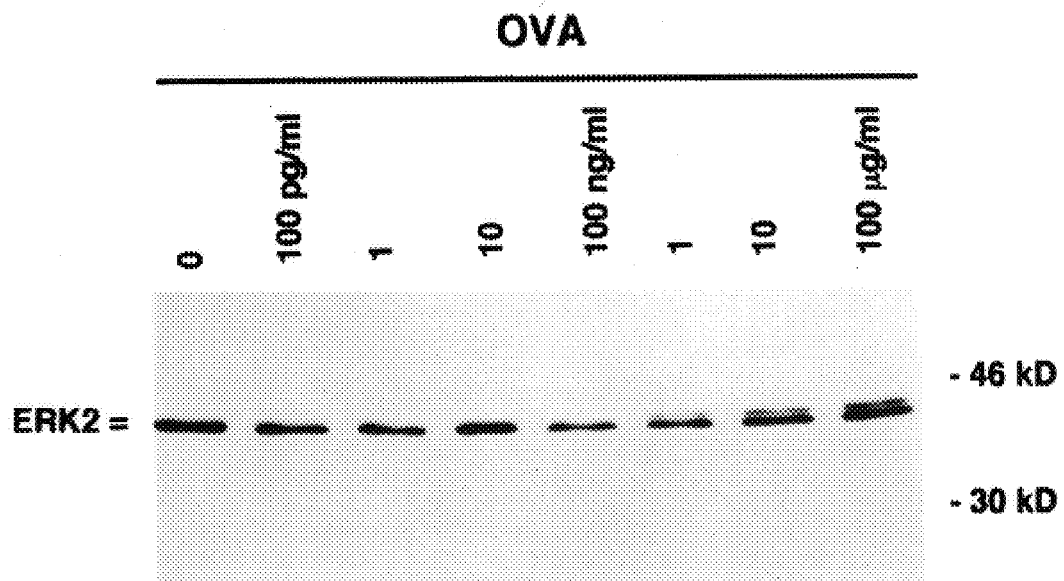
FIG. 4A shows an immunoblot demonstrating the activation of ERK2 by antigen in passively sensitized mast cells.
Figure 4B:
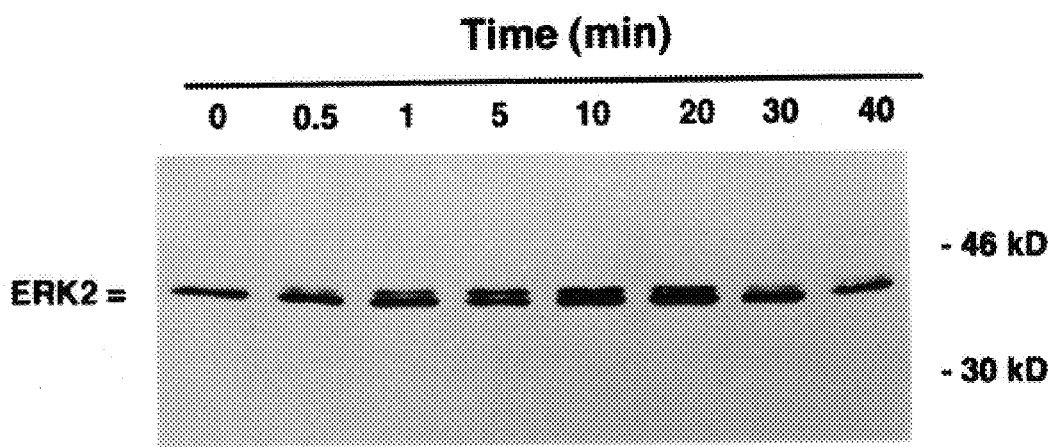
FIG. 4B shows an immunoblot demonstrating ERK2 phosphorylation measured in passively sensitized mast cells over time.
Figure 4C:
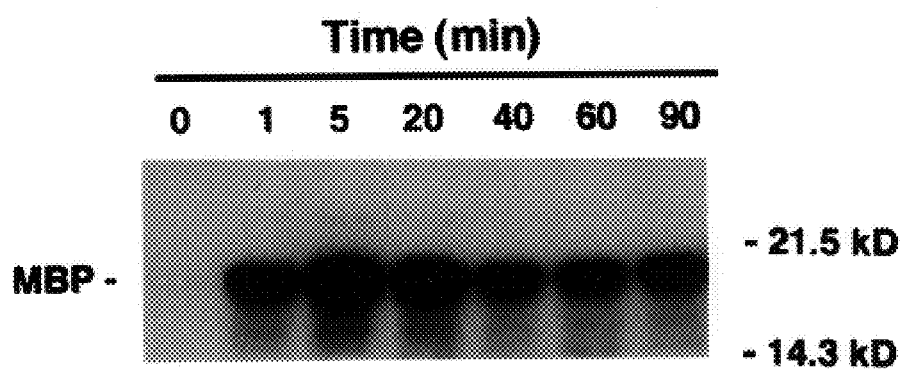
FIG. 4C shows an immunoblot demonstrating ERK2 kinase activity measured in passively sensitized mast cells for up to 90 minutes.

MC/9 cells sensitized with OVA-IgE were incubated with PBS (0) or 100 pg/ml to 100 μg/ml OVA for 1 min. Cell lysates were analyzed by SDS-10% polyacrylamide gel and immunoblotting using an anti-ERK2 antibody. ERK2 was phosphorylated in the presence of 1–100 μg/ml OVA (FIG. 4A). MC/9 cells sensitized with OVA-IgE were incubated with PBS (0 min) or 10 μg/ml OVA for 0.5, 1, 5, 10, 20, 30, or 40 min. ERK2 phosphorylation was elicited within 30 s, and a clear shift in mobility was observed at 1–20 min after 10 μg/ml OVA stimulation. Phosphorylated ERK2 protein was decreased 30–40 min after OVA addition (FIG. 4B). MC/9 cells sensitized with OVA-IgE were incubated with PBS or 10 μg/ml OVA for 1, 5, 20, 40, 60, or 90 min. Kinase activity of ERK2 was measured as $^{32}$P incorporation into myelin basic protein. ERK2 was significantly activated at 1 min after the addition of OVA, and its activation was maximal at 5–20 min. Significant activation was still observed at 90 min after OVA stimulation (FIG. 4C).

Example 4

The following example demonstrates that wortmannin inhibits JNK activation but not ERK2 activation.

Wortmannin was obtained from Calbiochem and stored as a 10 mM stock in dimethyl sulfoxide ($Me_2SO$).

Figure 5A:
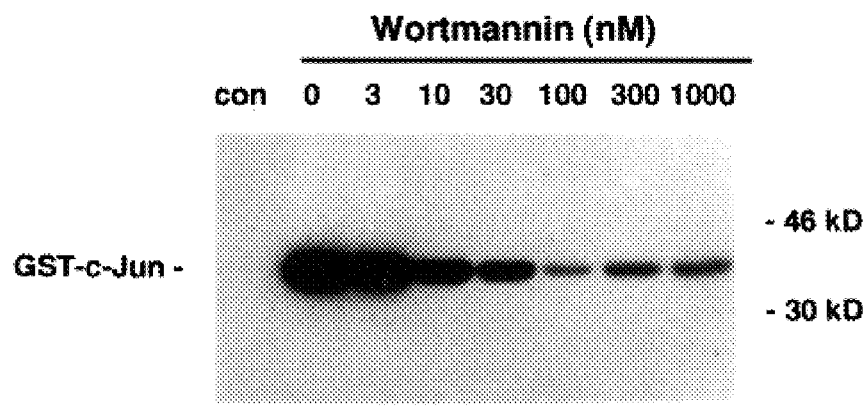
FIG. 5A shows an immunoblot demonstrating that wortmannin inhibits JNK activation by antigen in mast cells.
Figure 5B:
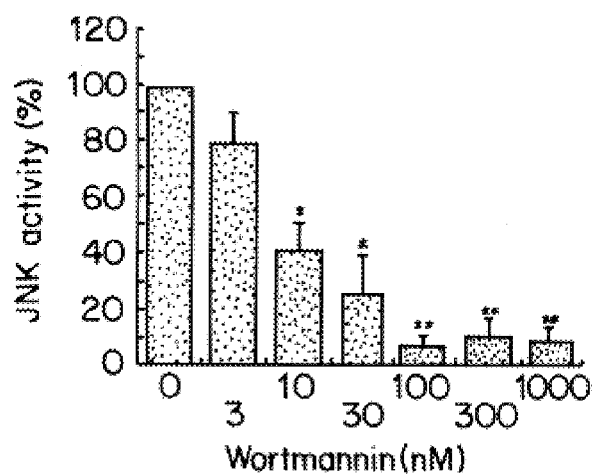
FIG. 5B demonstrates that a decrease in JNK activity correlates with increased wortmannin concentration.
Figure 5C:
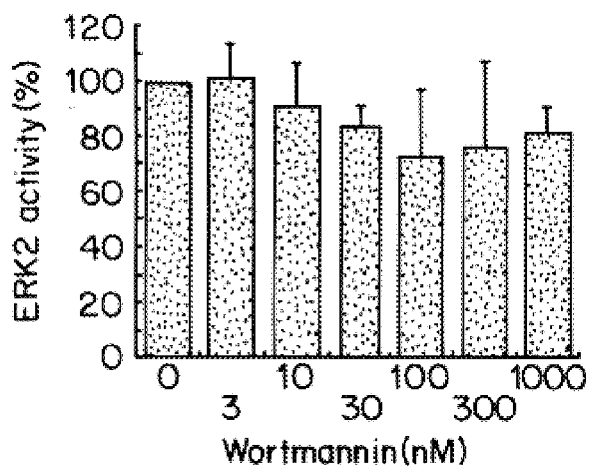
FIG. 5C shows that wortmannin does not inhibit ERK2 activity.

Wortmannin has been shown to inhibit PI3-kinase when used at concentrations below 1 μM. The effect of wortmannin (3 nM to 1 μM) on JNK and ERK2 activation induced by 10 μg/ml OVA stimulation in OVA-IgE-sensitized MC/9 cells was examined. MC/9 cells sensitized with OVA-IgE were incubated with 0.01% Me$_2$SO (control and 0 nM) or 3–1000 nM wortmannin for 15 min. The cells were then incubated with 10 μg/ml OVA or PBS (control) for 10 min. The data are expressed as the percentage of JNK activity detected in the presence of 10 μg/ml OVA and 0.01% Me$_2$SO (FIGS. 5A and 5B) or as the percentage of ERK2 activity stimulated by 10 μg/ml OVA in the presence of 0.01% Me$_2$SO (FIG. 5C). (*, p<0.05;**, p>0.01.)

Wortmannin inhibited JNK activity in a dose-dependent manner. The kinase activity in cells treated with 100 nM wortmannin was decreased to 8% of that observed in the absence of treatment (FIGS. 5A and 5B). In contrast, 100–300 nM wortmannin did not significantly inhibit ERK2 activation induced by OVA (FIG. 5C).

The aggregation of FcεRI initiates diverse signal transduction pathways. In addition to the release of mast cell granule contents, these pathways lead to late responses such as the increase in c-fos and c-jun expression and modulation of cytokine gene expression. Electrophoretic migration and activation of ERK2 was observed in antigen-stimulated MC/9 cells. Based on the present invention, it is believed that a role for ERKs in mast cells is the activation of cytosolic phospholipase A2, which would result in the production of arachidonic acid derivatives such as LTC4 and PGD2. Functionally, antigen-stimulated JNK activity in mast cells functions in the regulation of AP-1 activity and cytokine gene expression. The present invention provides the first evidence for the regulation of the MEKK/JNKK-contingent pathway, and not the ERK pathway, in mast cell cytokine production, thus permitting genetic analysis of the role of this pathway in mast cell biology.

Example 5

The following example demonstrates that TNF-α is generated by antigen in passively sensitized MC/9 cells.

Recombinant mouse TNF-α, purified rat anti-mouse TNF-α monoclonal antibody (ELISA Capture), and biotinylated rabbit anti-mouse TNF-α polyclonal antibody (ELISA Detection) were purchased from Pharmingen (San Diego, Calif.).

An ELISA for TNF-α production was performed as follows. Purified rat anti-mouse TNF-α monoclonal antibody was diluted to 2 μg/ml in coating solution (0.1M NaHCO$_3$, pH 8.2) and 50 μ was added to wells of an ELISA plate (Dynatech Laboratories). After overnight incubation at 4° C., wells were washed twice with washing solution (0.05% Tween-20/PBS) and blocked with PBS containing 10% FCS (10% FCS/PBS ) at room temperature for 2 hrs. After washing twice, standards (16 pg/ml–4 ng/ml recombinant mouse TNF-α) and samples were added at 100 μl per well and incubated overnight at 4° C. After washing four times, biotinylated rabbit anti-mouse TNF-α polyclonal antibody (1 μg/ml) was added to wells and incubated at room temperature for 45 min and wells were washed six times. 2 μg/ml avidin-peroxidase was added to wells, incubated at room temperature for 30 min, and wells were washed eight times. ABTS (2,2'-Azino-bis(3-ethylbenzthiazoline-6-sulfonic acid) substrate (30 mg/ml 0.1M citric acid, pH 4.35) containing 0.03% H$_2$O$_2$ was added at 100 μl per well and color reaction was allowed to develop at room temperature for 30 min. A plate was read at OD 410 nm and analyzed by Mycroplate Manager (Bio Rad, Hercules, Calif.).

Figure 6:
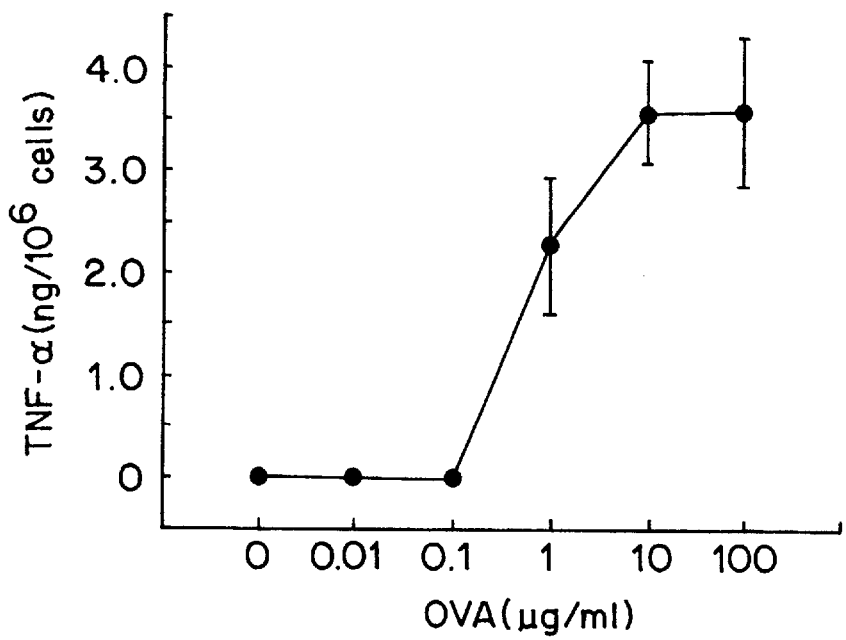
FIG. 6 demonstrates that TNF-a is produced in response to antigen by passively sensitized mast cells.

MC/9 cells (1×10$^6$/ml) were incubated with 500 ng/ml mouse monoclonal IgE specific for OVA (OVA-IgE) for 2 h. After washing, 1×10$^6$ sensitized MC/9 cells were incubated in the presence of 10 ng/ml to 100 μg/ml OVA for 3 h. After the incubation, the cell supernatant was harvested and TNF-α production was measured by ELISA. TNF-α production reached maximal by addition of 10 μg/ml OVA (mean±S.D., n=4). 1–100 μg/ml OVA induced TNF-α production at 3 h after addition of OVA (FIG. 6). 3.6 ng TNF-α was produced from 1×10$^6$ cells in the presence of 10 μg/ml OVA.

Figure 7:
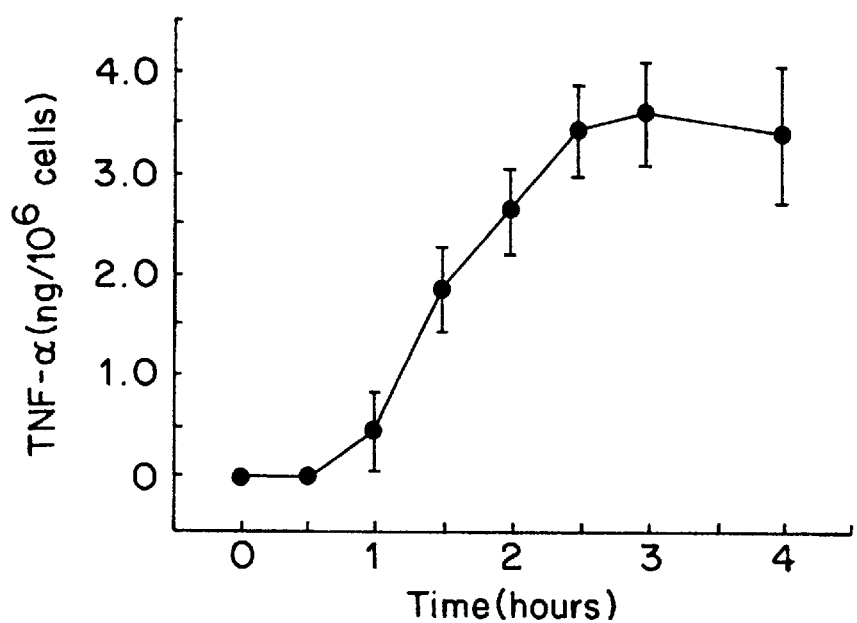
FIG. 7 shows the fold-increase in TNF-a production over time in response to antigen activation of passively sensitized mast cells.

MC/9 cells sensitized with OVA-IgE (1×10$^6$/ml) were incubated in the presence of PBS (0 h) or 10 μg/ml OVA for 0.5, 1.0, 1.5. 2.0, 2.5, 3.0, or 4.0 h. TNF-α was detected 1 h after addition of OVA and reached maximal at 2.5–3.0 h (mean ±S.D., n=4). TNF-α was not detected in the supernatant at 30 min after the addition of 10 μg/ml OVA. TNF-α production leveled at 2.5–3 hrs after the addition of OVA (FIG. 7).

The effects of a protein synthesis inhibitor, cycloheximide, and an RNA transcription inhibitor, actinomycin D, on TNF-α production were examined. 1 μg/ml cycloheximide or 1 μg/ml actinomycin D was incubated with cells 15 min before the addition of OVA. Both cycloheximide and actinomycin D completely blocked TNF-α production 3 h after stimulation (less than 30 pg per million cells) (data not shown).

The aggregation of FcεRI on mast cells is essential for the induction of allergic inflammation. Following aggregation, mast cells secrete a variety of preformed chemical mediators, such as histamine, and newly synthesized arachidonic acid derivatives. In addition to these biologically active substances, aggregation of FcεRI on mast cells leads to the production of cytokines and chemokines such as IL-3, IL-5, IL-6, TNF-α, GM-CSF, and MIP-1α. Among these cytokines, TNF-α, is produced in large amounts in mast cell lines. Both mouse bone marrow-derived mast cells and human cultured mast cells also produce TNF-α. Therefore, TNF-α is likely to be involved in allergic inflammation initiated by mast cell activation. TNF-α is a multifunctional cytokine which has effects in inflammation. Like other cytokines, TNF-α is newly synthesized following the aggregation of FcεRI on mast cells. Stimulation via the FcεRI markedly increases the levels of TNF-α mRNA in BMMC and some mast cell lines. The TNF-α gene shows the characteristics of an immediate-early gene in activated mast cells. It is strongly induced within 30 min in antigen-stimulated mast cells. MC/9, which does not have preformed TNF-α, produces TNF-α following the aggregation of FcεRI. The present inventors have shown herein that cycloheximide and actinomycin D completely inhibited TNF-α production induced by FcεRI aggregation, demonstrating that TNF-α is synthesized de novo following activation in MC/9 cells.

Example 6

The following example illustrates that p38 is activated by antigen in MC/9 cells.

MC/9 cells sensitized with OVA-IgE were incubated in the presence of PBS (0 min) or 10 μg/ml OVA for 1, 5, 15, 30, or 60 min. To immunoprecipitate p38 kinase, 3×10$^6$ cells were lysed by vigorous mixing in 0.4 ml of extraction buffer (1% Triton X-100, 10 mM Tris-HCl (pH 7.4), 5 mM EDTA, 50 mM NaCl, 50 mM MaF, 0.1% bovine serum albumin (BSA), 20 μg/ml aprotinin, 1 mM PMSF, and 2 mM Na$_3$VO$_4$). The lysate was incubated with the rabbit antiserum raised against the COOH-terminal peptide sequence of p38 (1:400 dilution) for 2 h at 4° C. Recombinant protein G sepharose 4B was added to the lysate and incubated for an additional 1 h at 4° C. The immunoprecipitates were washed once with extraction buffer, twice with PAN buffer (10 mM piperazine-N, N'-bis (2-ethanesulfonic acid) (PIPES, pH 7.0), 100 mM NaCl, 20 $\mu$g/ml aprotinin). For the in vitro kinase assay, the immunoprecipitates were suspended in 25 $\mu$l of assay buffer (25 mM Hepes, pH 7.4, 25 mM $\beta$-glycerophosphate, 25 mM NaCl$_2$, 2 mM dithiothreitol, 0.1 mM Na$_3$VO$_4$) containing a recombinant NH$_2$terminal fragment of ATF-2 (20–50 ng) as a substrate and 5 $\mu$Ci [$\gamma^{32}$P] ATP. The kinase reaction was terminated by the addition of 4×protein loading buffer, and the mixture was boiled for 5 min and separated by SDS-12% polyacrylamide gel. The gel was fixed with 5% acetic acid and 10% methanol solution, dried, and subjected to autoradiography. The kinase activity was quantified with a PhosphorImager (Molecular Dynamics, Sunnyvale, Calif.).

Figure 8:
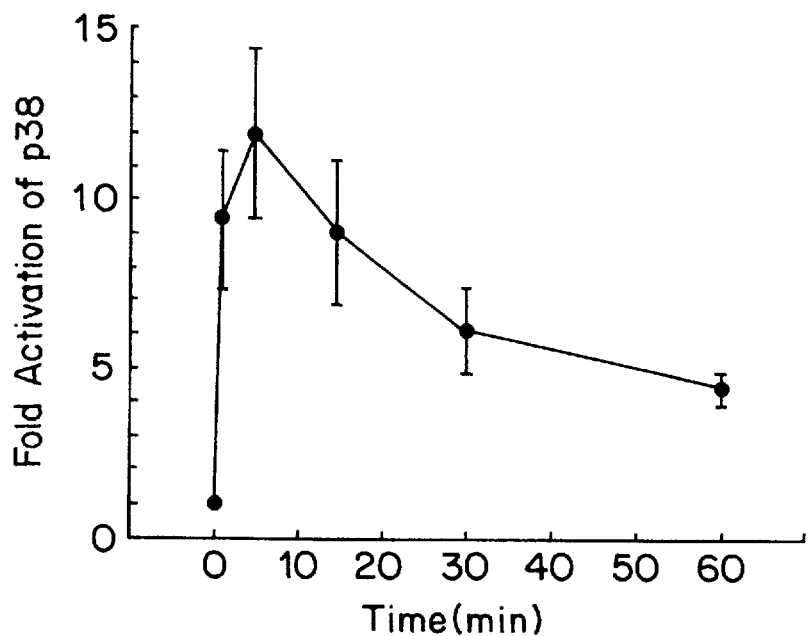
FIG. 8 demonstrates that p38 MAP kinase is activated in response to antigen activation of passively sensitized mast cells.

Following addition of OVA to MC/9 cells sensitized with OVA-IgE, p38 was significantly activated. OVA induced p38 activation in a dose-dependent manner (data not shown). p38 was significantly activated at 1 min and its activation was maximal (about 12-fold increase) at 5 min after the addition of OVA. p38 activities decreased gradually after 15–60 min (FIG. 8).

Example 1 demonstrates that JNK is strongly activated in mast cells following aggregation of FcεRI. This example demonstrates that another member of MAP kinase family, p38, the osmotic imbalance responsive kinase similar to the yeast Hog1 enzyme (#Lin) is also activated in mast cells by aggregation of FcεRI. p38, like JNK, is also activated by treatment of cells with pro-inflammatory cytokines and environmental stress such as extracellular changes in osmolarity. Its activation depends on dual phosphorylation on threonine-180 and tyrosine-182.

Example 7

The following example demonstrates that wortmannin inhibits both p38 MAP kinase activation and TNF-α production.

Figure 9:
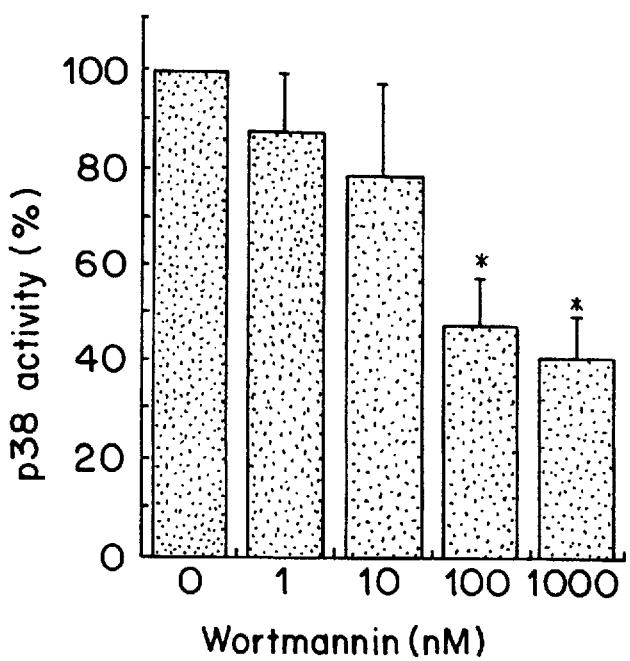
FIG. 9 shows that wortmannin inhibits p38 MAP kinase activation in activated MC/9 cells.

MC/9 cells sensitized with OVA-IgE(3×10$^6$) were preincubated with either 1–1000 nM wortmannin or a control (0.01% DMSO) for 15 min and stimulated for 5 min by addition of 10 $\mu$g/ml OVA. Wortmannin inhibited p38 MAPK activity in a dose-dependent manner. 100 nM-1 $\mu$M wortmannin significantly inhibited p38 MAPK activation (50–60% decrease in kinase activities) (FIG. 9). The data are expressed as the percentage of p38 activity detected in the presence of 10 $\mu$g/ml OVA and 0.01% DMSO (*, p<0.05). However, the inhibitory effects of wortmannin on p38 MAP kinase activation in stimulated MC/9 cells were not as strong as the inhibitory effects of wortmannin on JNK activation as shown in Example 4.

Figure 10:
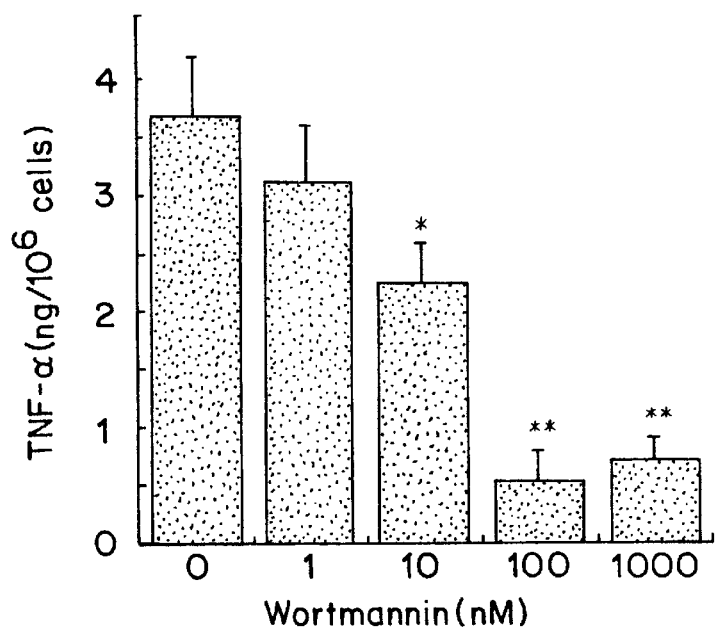
FIG. 10 demonstrates that wortmannin inhibits TNF-a production by activated MC/9 mast cells.

The effect of wortmannin on TNF-α production in MC/9 cells was also examined. MC/9 cells sensitized with OVA-IgE (1×10$^6$/ml) were incubated with 0.01% DMSO (control and 0 nM) or 1–1000 nM wortmannin for 15 min. The cells were then incubated with 10 $\mu$g/ml OVA for 3 h. TNF-α in the medium was measured by ELISA. 1 nM–1 $\mu$M wortmannin inhibited TNF-α production in a dose-dependent manner (mean±S.D., n=4,*, p<0.05;, p<0.01). TNF-α production was decreased by 77% in the presence of 100 nM wortmannin (FIG. 10**).

This example shows that p38 activation, like JNK activation, is significantly inhibited by the PI3-kinase inhibitor, wortmannin, treatment. PI3-kinase is an enzyme important in intracellular trafficking, actin polymerization, and growth factor signaling. PI3-kinase is activated following aggregation of FcεRI in a rat basophilic leukemia cell line, RBL-2H3. The inhibitory effects of wortmannin on JNK and p38 activation were observed in antigen-stimulated mouse bone marrow derived mast cells as well as MC/9 cells (data not shown). Wortmannin also inhibited TNF-α production of antigen-stimulated MC/9 cells in a dose-dependent manner. The concentrations of wortmannin which inhibited TNF-α production were similar to concentrations at which wortmannin inhibits PI3-kinase. These results indicate that inhibition of PI3-kinase by wortmannin decreases JNK and p38 activation following FcεRI aggregation and that activation of p38 can enhance the effects of the MEKK/JNKK-contingent pathway of the present invention on TNF-α production in antigen-stimulated mast cells.

Example 8

The following example illustrates that the MEK inhibitor, PD 098059, inhibits ERK2 activation, but does not inhibit TNF-α production, JNK activation, or p38 activation in MC/9 cells.

MEK inhibitor, PD#098059, was kindly provided by Dr. David Dudley (Warner Lambert Company, Ann Arbor, Mich.) and stocked 100 mM in DMSO. PD 098059 is a noncompetitive inhibitor of MAP kinase kinase (MEK). It exerts its effect by binding to the inactive form of MEK1.

MC/9 cells sensitized with OVA-IgE (1×10$^6$/ml) were incubated with 0.1% DMSO (control and 0 nM) or 3–30 $\mu$M PD 098059 for 1 h and the reaction was stopped by centrifugation at 5 min after the stimulation. The cells were then incubated with 10 $\mu$g/ml OVA or PBS (control) for 5 min. Kinase activity of ERK2 was measured as $^{32}$P incorporation into myelin basic protein (MBP).

1×10$^6$ cells were lysed in buffer (150 mM NaCl, 1% NP40, 0.5% deoxycholic acid sodium salt, 0.1% SDS, 50 mM Tris (pH 7.6), 10 $\mu$g/ml aprotinin, 5 mg/ml leupeptin, 1 mM PMSF). Samples were electrophoresed on SDS-10% polyacrylamide gels and proteins were transferred to nitrocellulose membranes. Membranes were incubated overnight in blocking buffer containing 1% BSA at 4° C. The monoclonal anti-ERK 2 antibody (200 $\mu$g/69 $\mu$l, Upstate Biotechnology) was added to the blocking buffer (1:1000) and blots were incubated for an additional 1 h at room temperature. The blots were washed in TBST (25 mM Tris, pH 8.0, 125 mM NaCl, 0.025% Tween 20) and specific reactive proteins were detected by an enhanced chemiluminescence method, employing a sheep anti-mouse Ig antibody linked to horseradish peroxidase (Amersham, Arlington Heights, Ill.).

In vitro kinase assay of ERK2 was carried out as described above with some minor modifications. 3 10$^6$ cells were lysed by vigorous mixing in 0.4 ml of lysis buffer (20 mM Tris-HCl (pH 8.0), 1% Triton X-100, 10% glycerol, 137 mM NaCl, 1.5 mM MgCl$_2$, 1 mM EGTA, 50 mM NaF, 1 mM Na$_3$VO$_4$, 1 mM PMSF, 5 $\mu$g/ml leupeptin, and 10 $\mu$g/ml aprotinin). The lysate was incubated with anti-ERK2 antibody (2 $\mu$g/ml) for 2 hrs at 4° C. Recombinant protein G sepharose 4B was added to the lysate and incubated for an additional 1 hr at 4° C. The immune complexes were washed three times with lysis buffer, and once with kinase buffer (30 mM Tris-HCl (pH 8.0), 20 mM MgCl$_2$, 2 mM MnCl$_2$). For the in vitro kinase assay, the immune complex suspension was incubated with 9 $\mu$g myelin basic protein (MBP) and 10 $\mu$Ci of [$\gamma$-$^{32}$P] ATP in kinase buffer in a final volume of 30

μl for 30 min at 30° C. The reaction was stopped by an additional 10 μl of 4×protein loading buffer. After the samples were boiled for 3 min, they were separated by SDS-12% polyacrylamide gel and stained with Coomassie brilliant blue, exhaustively destained, dried, and subjected to autoradiography. The bands corresponding to MBP were cut out of the gel, and radioactivity was determined by liquid scintillation counting.

Figure 11:
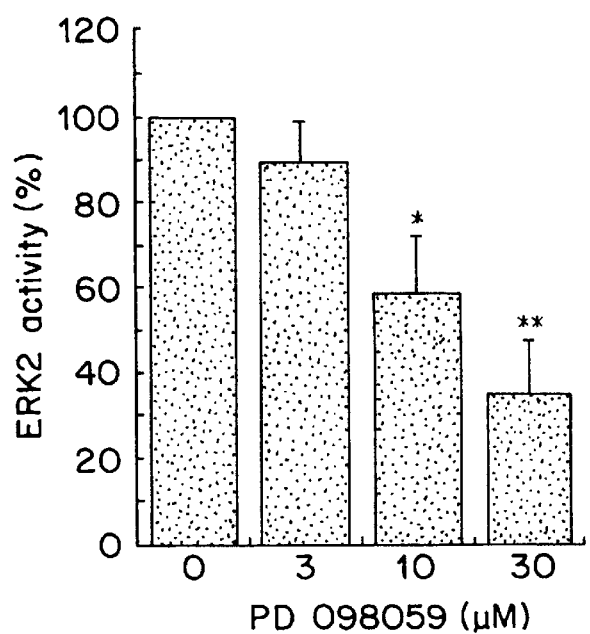
FIG. 11 shows that an MEK inhibitor, PD 098059, inhibits activation of ERK2 in activated MC/9 cells.

10–30 μM PD 098059 significantly inhibited ERK2 activities in MC/9 cells. OVA-induced ERK2 activity was decreased 65% in the presence of 30 μM PD 098059 (FIG. 11). The data are expressed as the percentage of ERK2 activity detected in the presence of 10 μg/ml OVA and 0.1% DMSO (*, $p<0.05$;**, $p<0.01$). However, PD 098059 did not inhibit JNK or p38 activation (data not shown).

Figure 12:
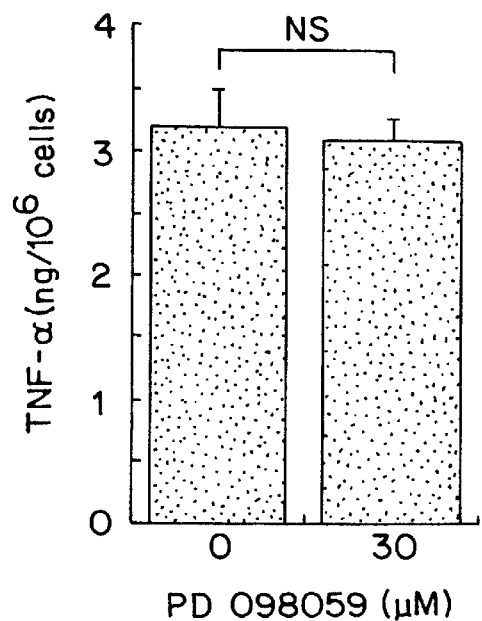
FIG. 12 shows that MEK inhibitor, PD 098059, does not inhibit TNF-$\alpha$ production in MC/9 cells.

MC/9 cells sensitized with OVA-IgE ($1\times10^6$/ml) were incubated with 0.1% DMSO or 30 μM PD 098059 for 1 h. The cells were then incubated with 10 μg/ml OVA for 3 h. TNF-α in the medium was measured by ELISA. 30 μM PD 098059 did not affect TNF-α production (mean±S.D., n=4, NS, no significance). In contrast to the effect seen with wortmannin in example 7, PD 098059 did not affect on TNF-α production at 3 h after addition of OVA (FIG. 12).

Cytokine production in mast cells via FcεRI is mediated by the phosphoinositide hydrolysis, an increase in intracellular calcium, and protein kinase C (PKC) activation because such production can be induced by calcium ionophore or the protein kinase C activator, PMA. MC/9 cells also produce cytokines including IL-2, IL-3, IL-4, and GM-CSF, after stimulation with PMA (phorbol myristate acetate) plus the calcium ionophore A23187. Prior to the present invention, it was thought that the Ras-dependent ERK signal transduction pathway was the intermediate in the transduction pathway leading to increases in gene transcription and proliferation in mast cells. ERKs phosphorylate specific transcription factors including members of the Ets family such as Elk-1. MEK inhibitor, PD 098059, selectively blocks the activation of MEK1 by Raf or MEKK in vitro. It exerts its effect by binding to the inactive form of MEK1, inhibiting both the phosphorylation and activation of ERK.

The present inventors have shown herein that PD 098059 strongly inhibited both ERK2 activity and phosphorylation induced by the aggregation of FcεRI in MC/9 cells. However, it did not inhibit TNF-α production, JNK activation or p38 activation. On the contrary, PD 098059 enhanced OVA-induced promoter activity of TNF-α although it did not enhance the TNF-α level in the medium. This demonstrates that ERK2 activation is not required for TNF-α production in mast cells. Without being bound by theory, the present inventors believe that ERK2 might be a negative regulator of transcription of TNF-α since inhibition of ERK2 activation enhanced activity of the TNF-α promoter in antigen-stimulated MC/9 cells.

Example 9

The following example demonstrates that wortmannin, but not PD 098059, inhibits TNF-α promoter activity in MC/9 cells stimulated by FcεRI aggregation.

The pXP1 plasmid containing full length of the human TNF-α promoter just upstream of the luciferase gene, designated pTNF(-1311)Luc, was provided by Dr. James S. Economou (Division of Surgical Oncology, UCLA School of Medicine, Los Angels, Calif.). pTNF(-01311)Luc was transfected into MC/9 by the DEAE-dextran method. $2\times10^6$ cells were washed once with 1×TBS (25 mM Tris, 137 mM NaCl, 5 mM KCl, 0.5 mM $Na_2HPO_4$, 0.49 mM $MgCl_2$, 0.68 mM $CaCl_2$, pH 7.5). Cells were suspended with 0.4 ml of 500 μg DEAE-dextran/4 μgDNA mixture and incubated at room temperature for 30 min. After washed with 1×TBS, cells were suspended with 10 ml of culture medium and plated on culture dish. After 24 h of the transfection, cells were passively sensitized with OVA-IgE and incubated with 10 μg/ml OVA for additional 15 h. In the experiment for cotransfection, 10 μg pCMV5MEKK$_{COOH}$, expression plasmid encoding MEKK$_{COOH}$, a truncated activated form of MEKK1 or 10 μg pCMV5, control empty plasmid, was transfected with 4 μg pTNF(-1311)Luc and transfected cells were harvested after 24 h of the cotransfection. For in vitro kinase assay, 4 μg or 10 μg pCMV5MEKK$_{COOH}$, or equivalent amount of control empty plasmid was transfected similarly and cells were harvested for in vitro kinase assay 24 h after the transfection.

Luciferase activity was measured to measure TNF-α promoter activity. Cell pellets were lysed in 200 μl of a buffer containing 25 mM Tris, pH 7.8, 2 mM EDTA, 2 mM dithiothreitol, 10% glycerol, 1% Triton X-100. 30 μl of the lysate was mixed with the same volume of Luciferase Assay Substrate containing beetle luciferin as a substrate (Promega, Madison Wis.), and chemiluminescence was measured for 30 sec as relative light units by a luminometer (Monolight 2010, Analytical Luminescence Laboratory, San Diego, Calif.).

Figure 13:
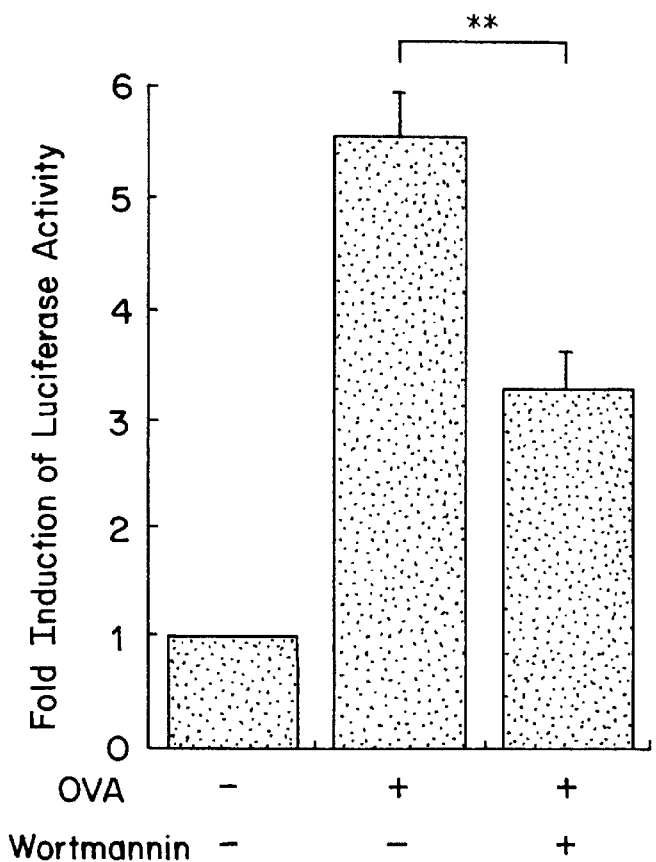
FIG. 13 demonstrates that the PI3-K inhibitor, wortmannin, inhibits TNF-A promoter activity in MC/9 cells stimulated by FceRI aggregation.
Figure 14:
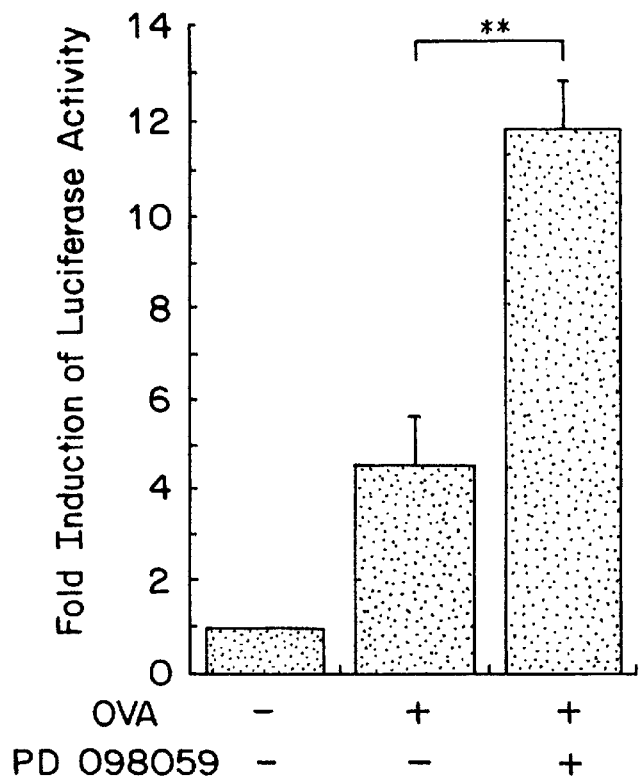
FIG. 14 shows that MEK inhibitor, PD 098059, enhances TNF-$\alpha$ promoter activity in MC/9 cells stimulated by FceRI aggregation.

MC/9 cells transiently transfected by pTNF(-1311)Luc were passively sensitized with OVA-IgE, and incubated for an additional 15 h with 10 μg/ml OVA or PBS in the presence of 0.01% DMSO or 100 nM wortmannin. Similarly, cells were incubated with 10 μg/ml OVA or PBS in the presence of 0.1% DMSO or 30 μM PD 098059. Luciferase activity in cell lysates was measured as relative light units (RLU) and standardized by control RLU (mean±S.D., N=4, $p<0.01$). OVA addition elicited a 5–6 fold induction of luciferase activity in the cells. 100 nM wortmannin significantly inhibited luciferase activity induced by addition of OVA (40% decrease in luciferase activity) (FIG. 13). In contrast to wortmannin, PD 098059 enhanced OVA-induced luciferase activity (FIG. 14). Therefore, the PI3-K inhibitor, wortmannin, inhibited TNF-a promoter activity in MC/9 cells, whereas the MEK inhibitor, PD 098059, enhanced TNF-a promoter activity.

Example 10

Figure 15:
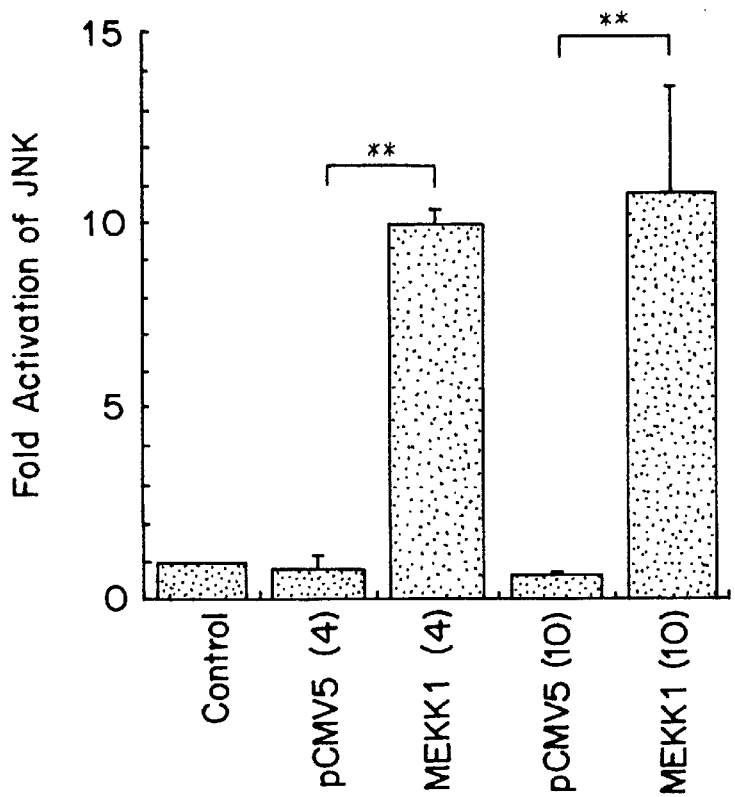
FIG. 15 demonstrates that overexpression of MEKK1 greatly enhances JNK activity in antigen-activated MC/9 cells.
Figure 16:
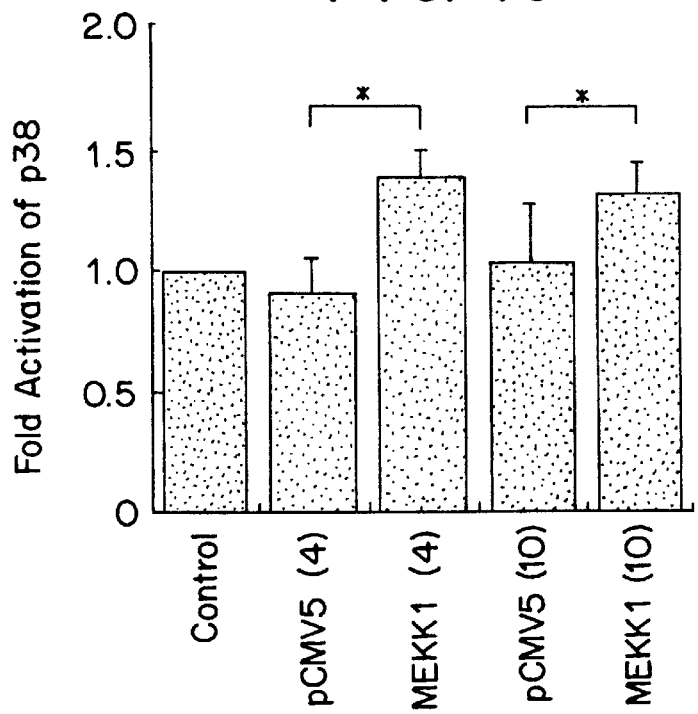
FIG. 16 shows that overexpression of MEKK1 weakly enhances p38 activity in antigen-activated MC/9 cells.

The following example demonstrates that overexpression of MEKK1 by MC/9 cells greatly enhances the activity of JNK and TNF-α promoter, weakly enhances p38 activity and ERK2 activity in antigen-activated MC/9 cells. 4 or 10 μg of pCMV5MEKK$_{COOH}$ (MEKK1(4) or MEKK1 (10)) or equivalent amount of pCMV5 empty plasmid (pCMV5(4) or pCMV5(10)) was transfected into MC/9 cells. Cells treated with only DEAE-dextran were used as a control. JNK activities (FIG. 15), p38 activities (FIG. 16), and ERK2 activities (data not shown) were measured at 24 h after the transfection. FIGS. 15–16 graphically show representative autoradiographs from each three of independent experiments. Kinase activities were standarized by control activity and expressed as fold-activation (mean±S.D., n=3,*, $p<0.05$;**, $p<0.01$).

JNK activity in the MC/9 cells transiently transfected by pCMV5MEKK$_{COOH}$ was strongly increased compared with the cells transfected by pCMV5 empty plasmid or treated with DEAE-dextran (Pharmacia Biotech, Uppsala, Sweden) alone. More than 11–15 fold increases of JNK activity was observed in pCMV5MEKK$_{COOH}$-transfected cells compared with pCMV5 empty plasmid-transfected cells (FIG. 15). In contrast, p38 activity was increased to a much lesser degree by the transfection of pCMV5MEKK$_{COOH}$ (FIG. 16). ERK2 was also activated by pCMV5MEKK$_{COOH}$ transfection. However, the degree of ERK2 activation was less than that of JNK (data not shown).

10 μg of pCMV5MEKK$_{COOH}$ (MEKK1) or 10 μg of pCMV5 empty plasmid (pCMV5) was transfected into MC/9 cells with 4 μg of pTNF(-1311)Luc. Luciferase activities were measured as relative light units at 24 h after the transfection.

Figure 17:
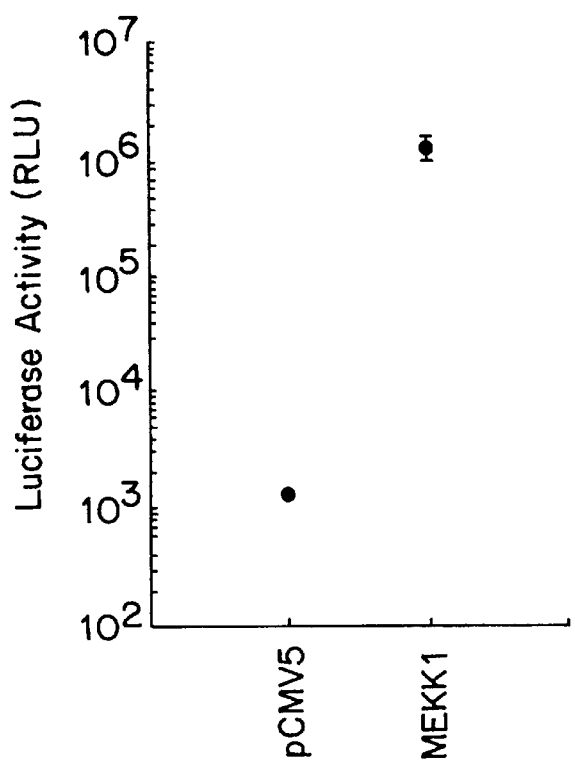
FIG. 17 demonstrates that overexpression of MEKK1 greatly enhances TNF-$\alpha$ promoter activity in antigen-activated MC/9 cells.

Cotransfection of pCMV5MEKK$_{COOH}$ and pTNF(-1311) Luc elicited a 1000-fold induction of luciferase activities compared with cotransfection of pCMV5 empty plasmid and pTNF(-1311)Luc, demonstrating that overexpression of MEKK1 results in an increase in the level of TNF-α promoter activity (FIG. 17).

A protein kinase cascade leading to activation of JNK is dependent on MEK kinase 1 (MEKK1). MEKK1 was identified as MEK-activating kinase unrelated to Raf-1. MEKK1 is activated in both a Ras-dependent and -independent manner. Examples 3A and 3B show, for the first time, that MEKK1 is also activated following the aggregation of FcεRI in MC/9 cells. Furthermore, the present inventors show herein that overexpression of MEKK1 strongly induces JNK activation and only weakly induces ERK activation.

JNKK activates both JNK and p38. As shown herein, however, JNK was strongly activated, but the activation of p38 was poor, in pCMV5$_{COOH}$-transfected MC/9 cells. overexpression of MEKK1 induced by transfection of pCMV5MEKK$_{COOH}$ enhanced the activity of TNF-α promoter strongly in MC/9 cells. Luciferase activity in pCMV5MEKK$_{COOH}$-transfected cells was 1000-fold higher than that in the cells transfected by control vector. These results demonstrate that activation of TNF-α promoter induced by MEKK1 overexpression is caused by JNK activation. Thus, MEKK1 and JNKK activation leading to JNK activation is directly involved in the gene transcription of TNF-α in antigen-stimulated because aggregation of FcεRI induces the activation of both MEKK1 and TNF-α promoter. Taken together, the above examples show that the MEKK/JNKK-contingent pathway is the primary signal transduction pathway leading to TNF-α production by mast cells, but other wortmannin sensitive pathways such as p38 can enhance such transcription of TNF-α in antigen-stimulated mast cells.

Example 11

Figure 18:
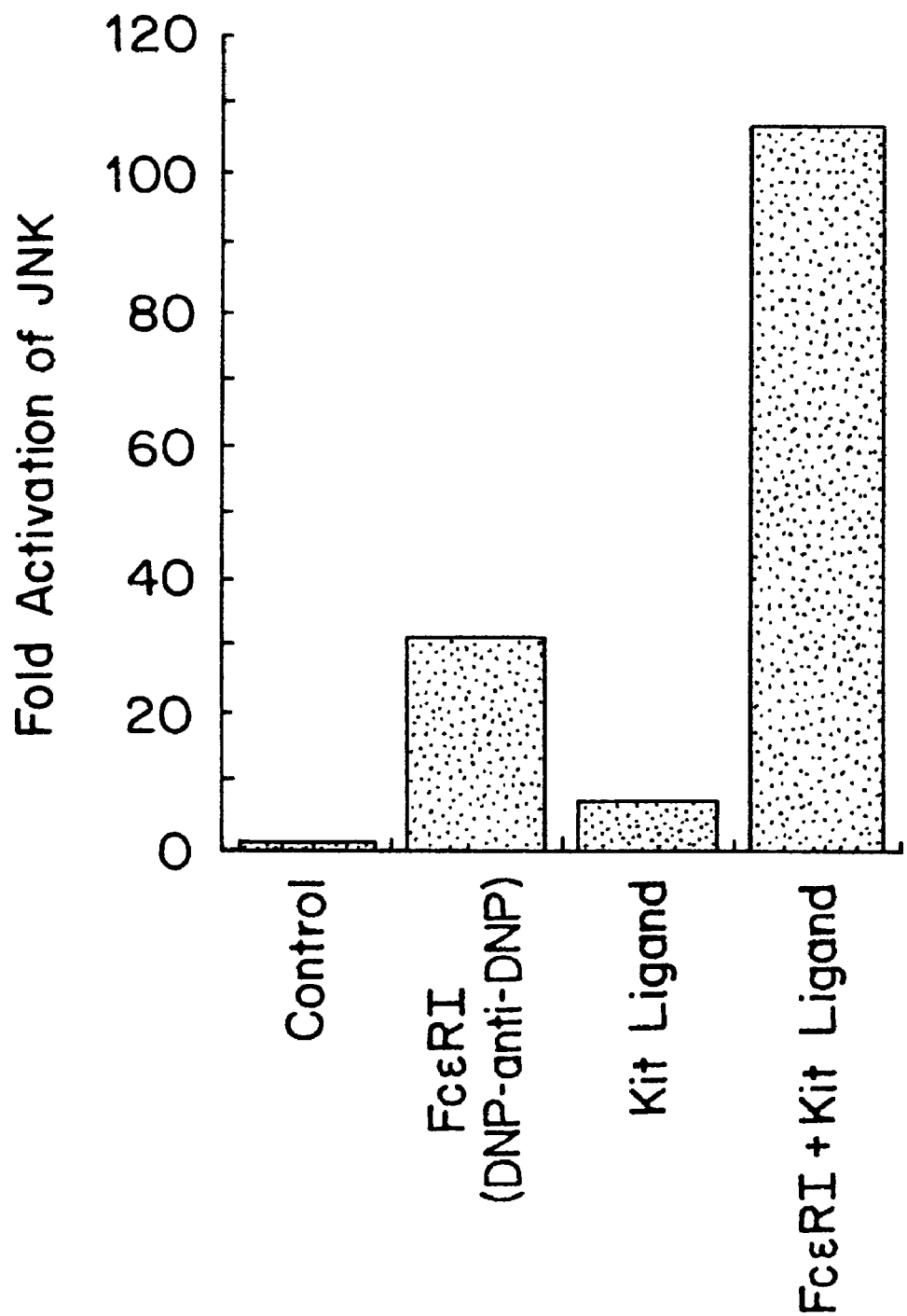
FIG. 18 demonstrates that cross-linking of c-kit on MC/9 cells synergizes with aggregation of FceRI to greatly enhance JNK activation.

The following example illustrates that cross-linking of c-kit on MC/9 cells synergizes with FcεRI aggregation to greatly enhance both JNK activation and TNF-a production. FIG. 18 shows that JNK activity is greatly enhanced in MC/9 cells activated by FcεRI aggregation. Cross-linking of c-kit by c-kit ligand in the absence of FcεRI aggregation only weakly activates JNK. However, when both c-kit and FcεRI are cross-linked, JNK activation is enhanced almost 4 fold above the level achieved with FcεRI aggregation alone.

Figure 19:
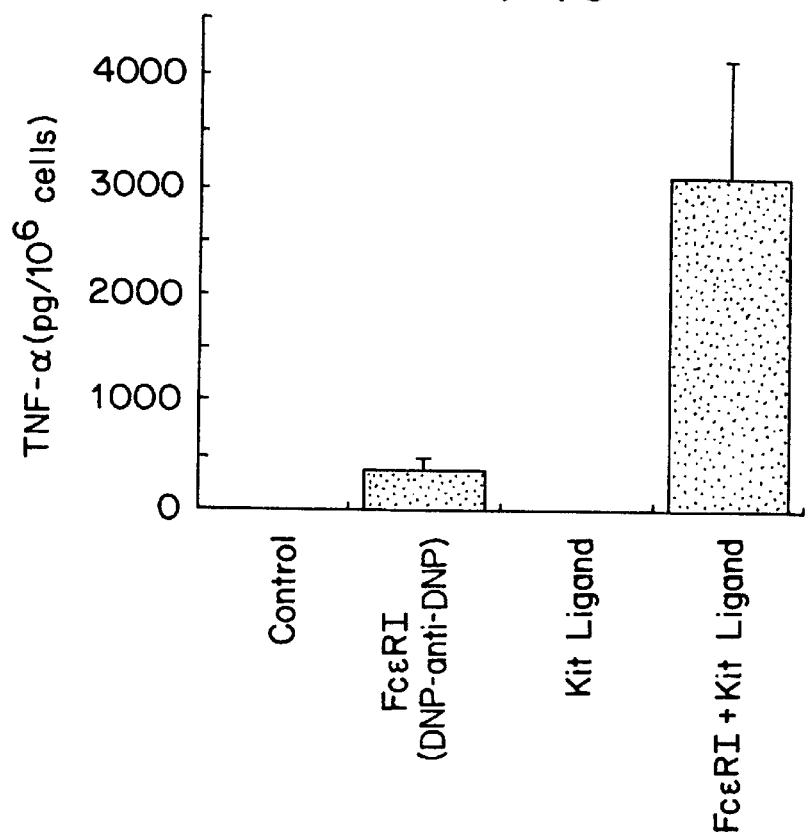
FIG. 19 demonstrates that cross-linking of c-kit on MC/9 cells synergizes with aggregation of FceRI to greatly enhance TNF-a production.

FIG. 19 shows the results of a similar experiment in which TNF-a production was measured. Like JNK, TNF-a production was greatly enhanced when both c-kit and FcεRI were cross-linked as compared to cross-linking either receptor alone.

Together, these experiments further demonstrate that activation of signal transduction by c-kit synergizes with FcεRI aggregation to activate the MEKK/JNKK-contingent signal transduction pathway of the present invention.

Example 12

Figure 20:
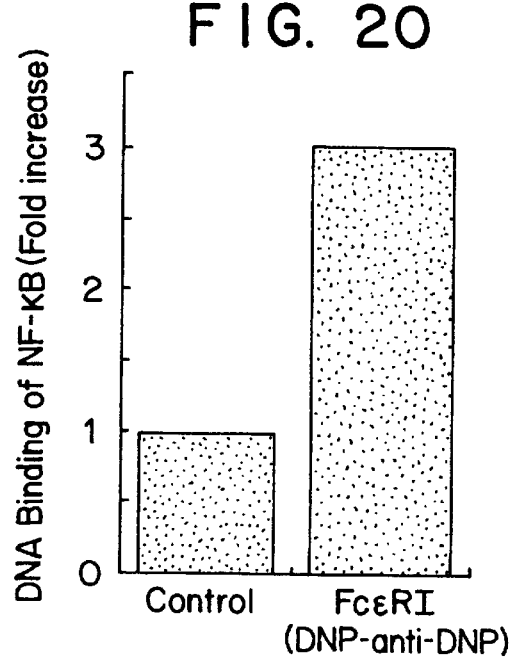
FIG. 20 shows that aggregation of FceRI on MC/9 cells activates the transcription factor, NFkB.

This example demonstrates that aggregation of FcεRI on MC/9 cells activates the transcription factor NFkB. FIG. 20 shows that cross-linking of FcεRI on MC/9 cells activates the transcription factor NFkB. Since NFkB is known to interact with various cytokine promoters to induce cytokine production, this example illustrates that FcεRI aggregation, which has been shown herein to induce the MEKK/JNKK-contingent pathway of the present invention, can activate transcription factors involved in cytokine production.

Another transcription factor, the nuclear factor of activated T cells (NF-AT) is essential for transcription of the IL-2 gene in activated T cells. Without being bound by theory, it is believed that NF-AT may be one in a family of related transcription factors that regulate the transcription of cytokine genes in mast cells as well as T cells because aggregation of the FcεRI induces NF-AT DNA binding activity in rat mast cells. NF-AT binding motifs are present in the promoter region of TNF-α genes as well as in the IL-2, IL-3, IL-4, and GM-CSF promoters.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A method to treat allergic inflammation in a human, comprising administering to said human an effective amount of a compound which directly interacts with a signal transduction molecule in an MEKK/JNKK-contingent signal transduction pathway selected from the group consisting of MEKK1, MEKK2, MEKK3, MEKK4, JNKK, JNK1, and JNK2, said interaction resulting in the inhibition of cytokine production such that allergic inflammation is thereby treated.

2. A method of using a hematopoietic cell to screen putative regulatory compounds for their ability to regulate cytokine production in said cell comprising:

provide a hematopoietic cell having an MEKK/JNKK-contingent signal transduction pathway;

contacting said cell with a putative regulatory compound; and determining whether said putative regulatory compound is capable of modulating the amount of cytokine produced by said cell, wherein said cell lacks an ERK-dependent signal transduction pathway.

* * * * *